United States Patent [19]
Lehrer

[11] Patent Number: 5,536,273
[45] Date of Patent: Jul. 16, 1996

[54] APPARATUS AND METHOD OF EXTRACORPOREALLY APPLYING AND LOCKING LAPAROSCOPIC SUTURE AND LOOP LIGATURES

[76] Inventor: Theodor Lehrer, 936 Intracoastal Dr., Apt 21C, Ft. Lauderdale, Fla. 33304

[21] Appl. No.: 164,462

[22] Filed: Dec. 9, 1993

[51] Int. Cl.⁶ .................................................. A61B 17/04
[52] U.S. Cl. ......................... 606/139; 606/144; 606/148; 289/1.5; 289/17
[58] Field of Search ................................ 606/139, 144, 606/147, 148; 289/1.2, 1.5, 2, 17

[56] References Cited

U.S. PATENT DOCUMENTS

| | | | |
|---|---|---|---|
| 3,344,790 | 10/1967 | Dorner | 128/340 |
| 3,871,379 | 3/1975 | Clarke | 128/326 |
| 4,493,323 | 1/1985 | Albright et al. | 128/340 |
| 4,597,390 | 7/1986 | Mulhollan et al. | 128/340 |
| 4,614,187 | 9/1986 | Mulhollan et al. | 128/303 R |
| 4,760,848 | 8/1988 | Hasson | 128/340 |
| 4,945,920 | 8/1990 | Clossick | 128/751 |
| 5,015,250 | 5/1991 | Foster | 606/147 |
| 5,037,433 | 8/1991 | Wilk et al. | 606/139 |
| 5,129,912 | 7/1992 | Noda et al. | 606/139 |
| 5,147,373 | 9/1992 | Ferzli | 606/144 |

OTHER PUBLICATIONS

Graumont & Hensel, *Encyclopedia of Knots and Fancy Ropework*, New York 1945, preface & pp. 11, 56, 99–101.

*Primary Examiner*—Gary Jackson
*Attorney, Agent, or Firm*—John C. Smith

[57] ABSTRACT

A suture applier instrument for tying suture and loop ligatures in laparoscopic excisional procedures such as LAVH, tubal ligation, salpingectomy, cophorectomy and appendectomy; in the repair of the fallopian tubes, uterus and ovaries; and in retropubic colposuspension using locking slip knots; and an efficient extracorporeal method to effectively lock them. The slip knot is held at the tip of the suture applier instrument and is kept in position on the target tissues while its two suture strands are operated extracorporeally, tying the loop ligature with one of the strands and locking or tightening the knot itself with the other. Additional hitch knots may be introduced and tied after the slip knot has been applied, using the same instrument. New knots, spool for pretied knot sutures and knot tying techniques for use with the suture applier are presented.

10 Claims, 18 Drawing Sheets

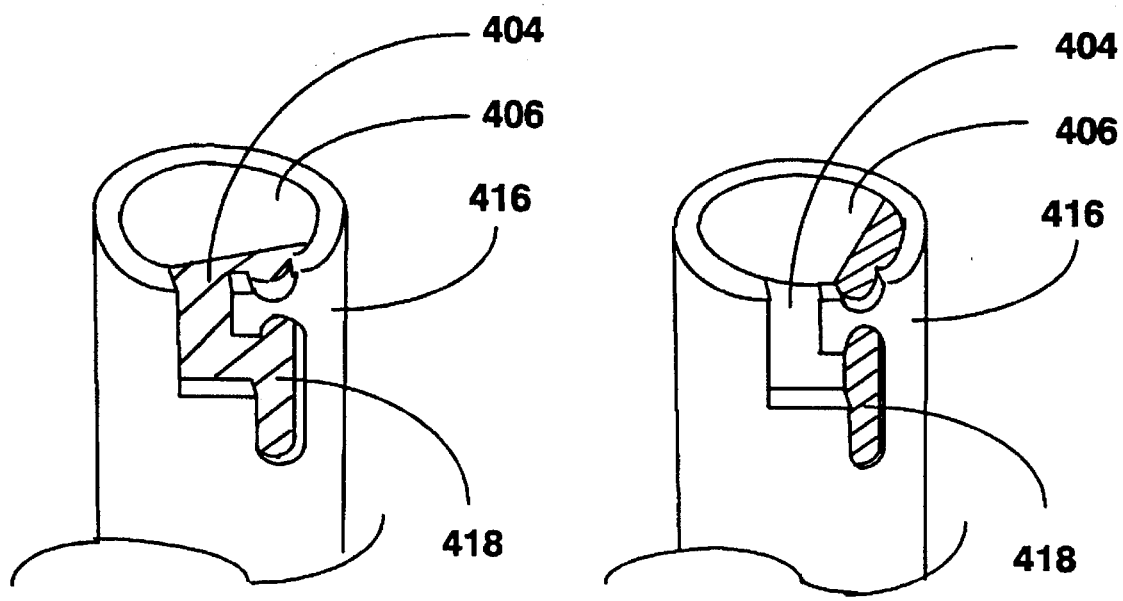
Figure 5A  Figure 5B
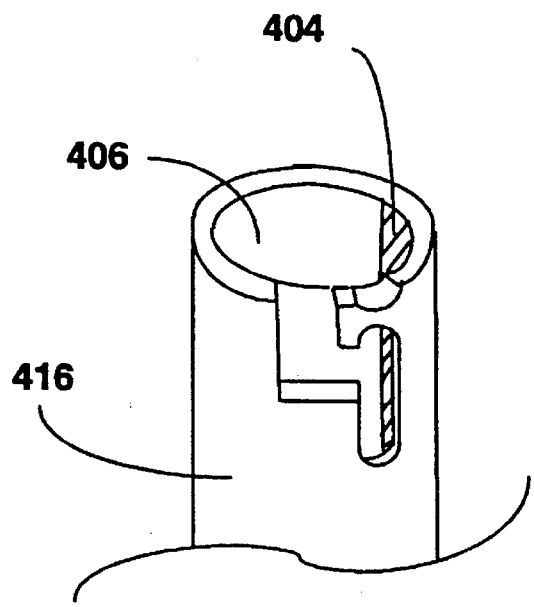
Figure 5C

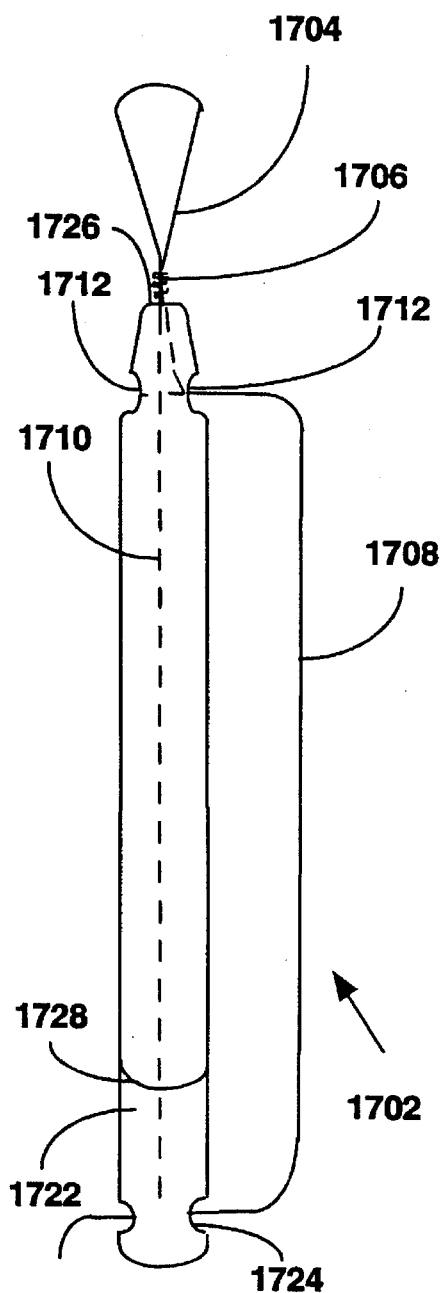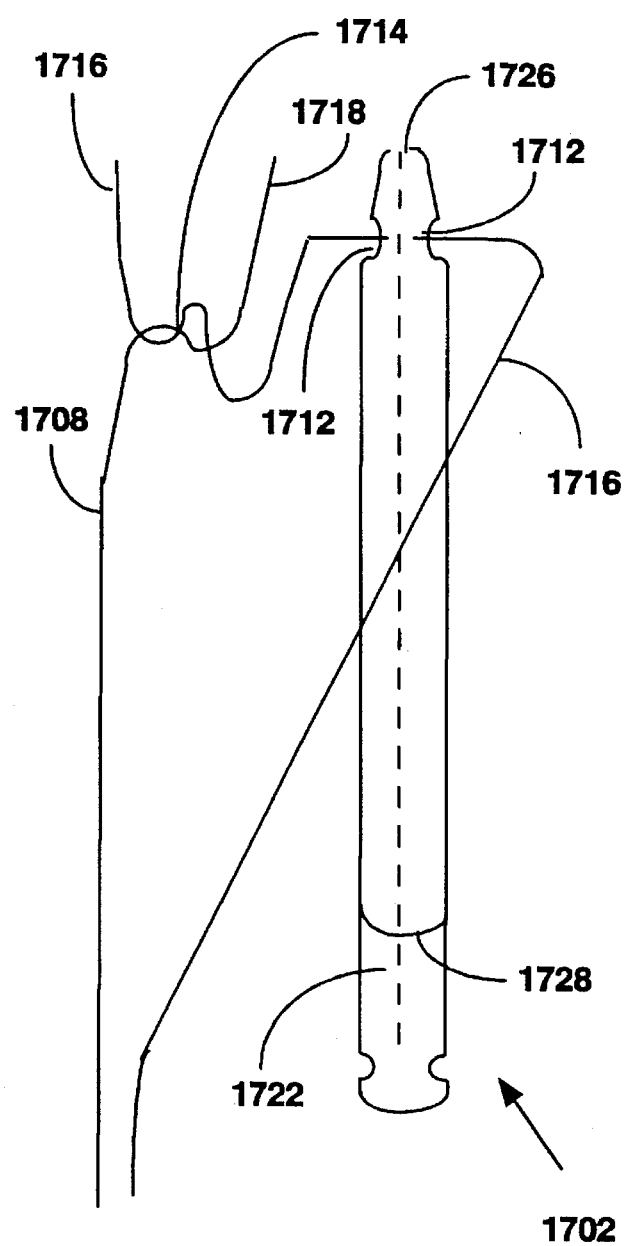
Figure 17A   Figure 17B

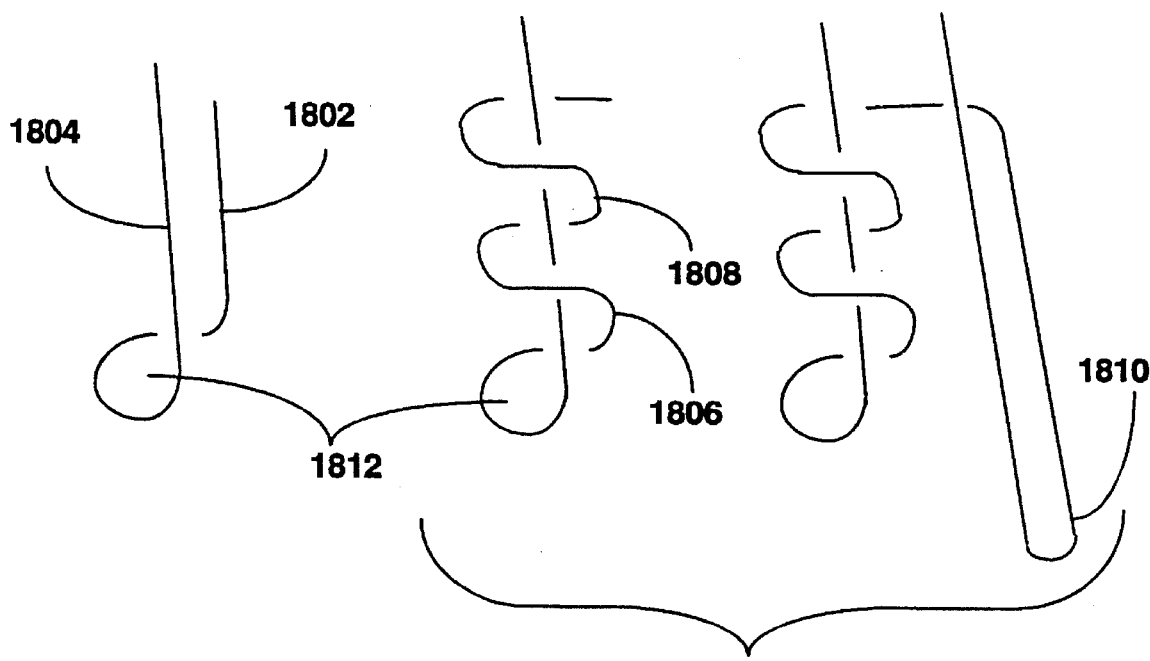
Step 1    Step 2
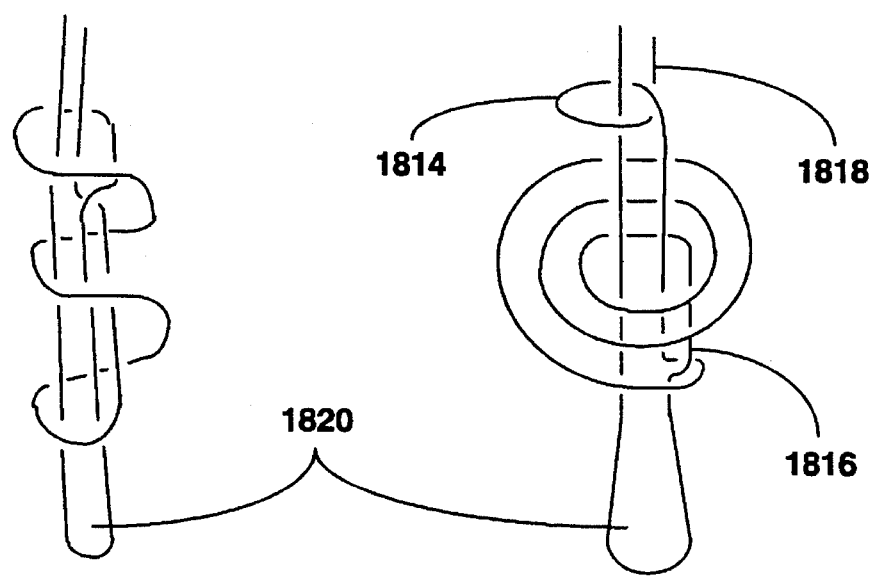
Step 3    Step 4
Figure 18

APPARATUS AND METHOD OF EXTRACORPOREALLY APPLYING AND LOCKING LAPAROSCOPIC SUTURE AND LOOP LIGATURES

BACKGROUND OF THE INVENTION

1. Technical Field

The present invention relates to surgical instruments. In particular, instruments used for the extracorporeal application of non-locking and locking slip knots to endoscopic suture and loop ligatures.

2. Background Art

A wide variety of endoscopic surgical techniques for securing tissue has been developed. In addition to the suture and loop ligature methods which are the subject matter of this invention, alternative techniques to the suture and/or ligature method include the use of mechanical devices such as staples, silastic rings and clips, automatic stapling devices, electrosurgery and lasers. A high proportion of endoscopic surgeons experience difficulty in acquiring and maintaining proficiency in their use. These alternate techniques are costlier and may be associated with technical problems, more extensive tissue damage and other surgical complications.

While great advances have been made to improve them over time, improvements in endoscopic suture and loop ligatures are highly desirable because this is the preferred technique in open surgery, which is the standard for operative laparoscopy. Surgeons have mastered the suture method in open surgery and have trusted it over many years to be the most reliable and cost effective technique.

The suture method is superior at repairing organs after portions have been excised from them. For instance, as in a myomectomy procedure, the uterus can be restored. Further, in tubal reconstructive surgery, the patency of the fallopian tube can be best restored with suturing techniques. Procedures to elevate the bladder and correct urinary incontinence are likewise best done with the suture method.

Suturing is a superior technique to effect hemostasis, particularly of large blood vessels. It provides precision in handling the tissues, which is often required when operating in areas where the bowel, ureter, or other structures may be dangerously close to the operative site, particularly in cases where the anatomy has been distorted by adhesions, tumors, endometriosis, or inflammation.

Automatic gun staplers are too wide and rigid in shape, and may lack the precision that is required on the aforementioned surgical conditions.

In this regard, the problem with electrosurgery is the so called "field effect" that is produced by the spread of heat, which destroys a wider sector of tissues around the target. When used to effect hemostasis of large vessels, electrosurgery frequently causes extensive tissue damage.

Another example of the more extensive tissue damage of electrosurgery as compared to sutures is in tubal ligation. For electrosurgery to be effective and reliable, the surgeon must completely coagulate at least three centimeters of the tube. With the suture method, only one centimeter of the tube is taken out, which is advantageous in the event that the patient requires a tubal reanastomosis to be performed in the future. An additional advantage is that a specimen is obtained that can be examined histologically.

Silastic rings may slip off the fallopian tube, producing a failed tubal ligation.

Securing surgical ties is standard practice in open laparotomy surgery. In this form of surgery, the surgeon has wide and direct access to the operative site and can secure surgical ties with relative ease. As a result, the surgeon in this type of operative environment has great flexibility in how ligatures are applied and secured.

While this provides advantages to both the surgeon and patient, there are also serious drawbacks to this type of surgery. In particular, the size of the incision required to effect access by the surgeon creates scarring which may be of significant concern to the patient. In addition, larger incisions create larger areas which not only are injured by the incision and require greater effort to heal, but also create more potential areas of infection, more post operatory pain, and more respiratory, urinary, and gastrointestinal difficulties that may prolong the convalescence period.

One solution to these problems has been provided by the development of laparoendoscopic surgery. In this type of surgery, an illuminated tubular instrument, a laparoscope, is passed through a puncture wound in the abdomen. The laparoscope typically is used not only for examinations, but also for a variety of surgical procedures (e.g., tubal ligations, removal of tumors of the ovaries or uterus, etc.). One of the principle advantages of a laparoscope is the reduced size of the incision required to effect the surgery. Further, depending on the surgical procedure being performed, residual scarring may effectively be reduced, as well as post operatory complications. The foregoing advantages mean that hospital stays may be reduced and/or eliminated, making outpatient ambulatory surgery possible. The cost of surgery may be therefore lower and full recovery faster.

While prior approaches to laparoscopic surgery have produced the aforementioned benefits to patients, they have had an adverse effect on the surgeons flexibility in adequately applying available suturing techniques for a given situation. In particular, the limited use of the suture method in laparoendoscopic surgery is due to the difficulties that surgeons currently encounter in locking their ties. The Surgeon's Knot and/or hitch knots are well known in the art and are the type of knots most frequently used in operative laparoscopy, but these knots have a tendency to loosen up before a second throw can be made, which may render the tie ineffective. In comparison, slip knots have better slipping strength. Non-locking slip knots have less slippage power than self locking slip knots. This difference in slippage power increases after the noose is tied proportionally to the force applied on the standing part suture that closes it.

Prior art ligator devices have been developed which use slip knots. The slip knots currently in use in commercially available loop ligature and suture ligature kits are the Roeder loop, and the Duncan loop. Both of these knot types are well known in the art. The problem with using the Roeder loop, and to a lesser degree the Duncan loop, is that they are not effectively locked and the tie needs to be secured with an additional knot.

Another problem associated with the design used for these slip knots is that the manufacturers typically trim the end suture strand too short (i.e., very close to the knot). As a result, the noose of the slip knots can be tightened but not the knot itself. For this reason, the surgeon cannot restore the loss of slippage power of the knot that occurs when the noose is applied on the tissues. In addition, the slip knots cannot be effectively locked without pulling the end portion of the suture against the knot. Therefore, the prior art Roeder and Duncan loops whose end portions are trimmed will remain unlocked on the tissues.

An example of this slippage is shown in study by Hay et al (Hay D L, Levine R L, von Fraunhofer J A, Masterson B J. Chromic gut pelviscopic loop ligature: Effect of the number of pulls on the tensile strength. J Reprod Med 1990, 35:260-2) (hereinafter, Hay). In this study, it was demonstrated under laboratory conditions that with a commonly known knot called the Roeder loop, the least slippages occurred when only one pull was used to apply the loop ligature. In the study, two out of five loop ligatures had slippage with one pull. However, the slippage rate increased with each additional pull to three out of five; and to four out of five loop ligatures tested.

This problem is more apparent when newer materials, such as polyglactin (Vicryl Dexon), polydioxanone (PDS) or poliglecaprone (Monocryl) are used. These suture materials have comparatively less slippage power than catgut. However, catgut is a highly reactive material which is being replaced. The advantage of the newer materials is that they cause less foreign body inflammatory reaction and may be potentially better than catgut, provided that the suture or loop ligature is properly secured.

In addition to the problem discussed above (i.e., the inability of prior art knots to tighten the knot itself, and then lock the knot due to the excessively trimmed end portion of the suture), the excessively short end suture strand also precludes locking the slip knot with an additional security knot. To compensate for this potential problem, Hunt advises using three loop ligatures to tie pedicles such as a fallopian tube (Hunt R. Atlas of Female Infertility Surgery, Second Edition, 1992 Mosby Year Book. Page 264–267). These multiple ligatures are not locked. Of course, each ligature increases the devascularization of tissue and inflicts some tissue damage when applied. This brings about an increase of inflammation secondary to the resorption of devitalized tissue that must be eliminated and a foreign body inflammatory reaction to the excess suture material, with the possibility of adhesions and of secondary intestinal obstruction. Therefore, the application of three ligatures may result in some additional damage to the ligated tissue and other intraperitoneal organs.

Surgeons would prefer to avoid using multiple ligatures as long as they can rely on the fewer ligatures remaining securely tied. If a single tie is properly locked, as in open surgery, the surgeons seldom feel the necessity to add multiple ligatures on a single pedicle. Unless ligature manufacturers stop trimming the end of the suture, surgeons need to make their own suture and loop ligatures, leaving enough length of end suture to add a security knot using either an intracorporeal or extracorporeal tying technique. Intracorporeal tying techniques are difficult to master to a degree comparable to open surgery, and can be quite time consuming to perform. Making the knot intracorporeally, and tying it with the appropriate tension is more difficult and time consuming to the surgeon which in turn creates higher cost to the patient. Further, the reduced efficiency of the surgeon and the increase in time taken to complete the surgery means that the patient is exposed for a longer period of time to the stress of surgery and anesthesia and increases the cost of surgery. This may in turn negate the benefits of laparoscopic surgery and create a logistical problem for busy surgical facilities and personnel in terms of manpower efficiency which also increases patient costs.

Therefore, this intracorporeal knot technique, while addressing some of the problems caused by slippage, has drawbacks which create both economic inefficiencies and health risk, both of which will ultimately be borne by the patient. Extracorporeal knot tying is more efficient and easier for the surgeon to master. By enabling the surgeon to more quickly complete the surgery, the patient is spared the aforementioned potential problems of intracorporeal knot tying.

The prior art has not recognized that leaving both suture strands sufficiently long to span the distance from the target tissues to the outside makes it possible to extracorporeally tighten slip knots and restore the slippage power; and to lock a self locking slip knot. In addition, it provides the endoscopic surgeon the ability to secure the loop ligature with extracorporeal knots, as in open surgery, avoiding the necessity of using multiple ligatures on a single pedicle.

The use of slip knot for suture ligatures has the additional problem of the "sawing effect" in which the suture that is passed through the tissues slides against the tissues and damages them much like a rope can damage the skin of the hands holding it. Those skilled in the art will recognize that the sawing effect only applies to suture ligatures. In a loop ligature, the suture material surrounds the tissue and, therefore, will not saw through it. One known technique that takes advantage of the superior holding power of a slip knot and can decrease the sawing effect that a slip knot may produce upon initial tightening is to first pass the suture needle that is attached at the end of one of the suture strands of the slip knot, first through the tissues that are being suture ligated, and then through the noose of the slip knot that has been introduced into the peritoneal cavity together with the suture needle. In this needle-thru-noose technique, the suture needle may be placed on the suture strand that controls the closure of the noose, which is called the "standing part" or similarly, the suture needle may be placed on the other suture strand, which is called the "end portion". These two approaches are useful, but limited because their ties remain unlocked. In addition, the ready made suture kits using these two approaches have a limited availability of suture materials and needle sizes.

The same can be said of the pretied suture method that is commercially available as the "Pretied Endoknot Suture" from Ethicon, Inc., which consists of a suture needle that is attached to the standing part and is passed first through the tissue and then through the noose of a wire guide which is then pulled back passing the standing part into the lumen of the tubular ligator and out through the proximal opening of the tubular ligator. The loops of the knot, that are pretied around the shaft of the tubular ligator are then advanced over its distal end to form a knot. This pretied method of the prior art can save time and avoid errors when fashioning the knots. However, since the knot is completed extracorporeally and then reintroduced, the large noose that extends from the knot to the target tissues requires more suture material to pass under tension through the tissues. This represents no advantage in terms of the sawing effect on tissues upon initial tightening of the slip knot when compared to prior art methods of fashioning and/or delivering an extracorporeal slip knot.

Thus, the drawback to the Pretied Endoknot Suture technique is that the knot must be completed outside the peritoneal cavity and then reintroduced. The large resulting noose extends from the outside to the target tissues which therefore requires more suture material to pass through the tissues, under tension, producing the so called "sawing effect." The large size of the noose creates more trauma to the tissue as more suture material is passed through it to close the noose as compared to the small size noose of an intracorporeal knot.

While the prior art has addressed many of the problems associated with ligature application, it has failed to provide surgeons the ability to effectively use the full spectrum of suture knots without adverse side effects, such as the "sawing effect" or tie slippage problems discussed above. In particular, the prior art has not provided the means to most effectively and efficiently employ endoscopic suture ligatures and loop ligatures by using slip knots that have better slippage power and may lock themselves; has not provided ligator devices and slip knots with suture strands sufficiently long to be manipulated extracorporeally to allow tightening and locking the knot itself after it is applied on the target tissues, and allow the ties to be further secured with additional extracorporeal knots as is done in open surgery. The prior art has not provided easy extracorporeal tying techniques for suture ligatures that use slip knots without a "sawing effect" on tissues. Particularly, the prior art has not provided the means to complete intracorporeally the knot of the pretied knot suture forming a noose of small size that can be tied with a negligible amount of sawing effect on the tissues, if any.

SUMMARY OF THE INVENTION

The invention disclosed herein is a rapid loading ligature application system having loop and suture ligature appliers which deliver well locked slip knots as the first throw of the ligature which it can further secure with extracorporeal knots. This is possible because of the lengthened suture strands used with the ligature application system. Five new knots with superior slipping power are introduced. Loop ligatures are provided with a lockable ready made slip knot. Suture ligatures use two types of spools which employ pretied knots for use with various embodiments of the ligature application system or which can be mounted on the needle driver. The pretied knot suture ligatures can form the knot either inside or outside of the body cavity. If formed inside the body cavity, the noose is small and substantially reduces the sawing effect.

BRIEF DESCRIPTION OF THE DRAWINGS

FIGS. 5A–5C are detailed views of the distal end of the ligator device of FIG. 4.

FIGS. 17A–17B show a loop ligator applier with one of the Lehrer knots in ready made form.

FIG. 18 is a diagram showing the alternative method of fashioning the knots shown in FIG. 1.

DESCRIPTION OF THE PREFERRED EMBODIMENT

Figure 1:
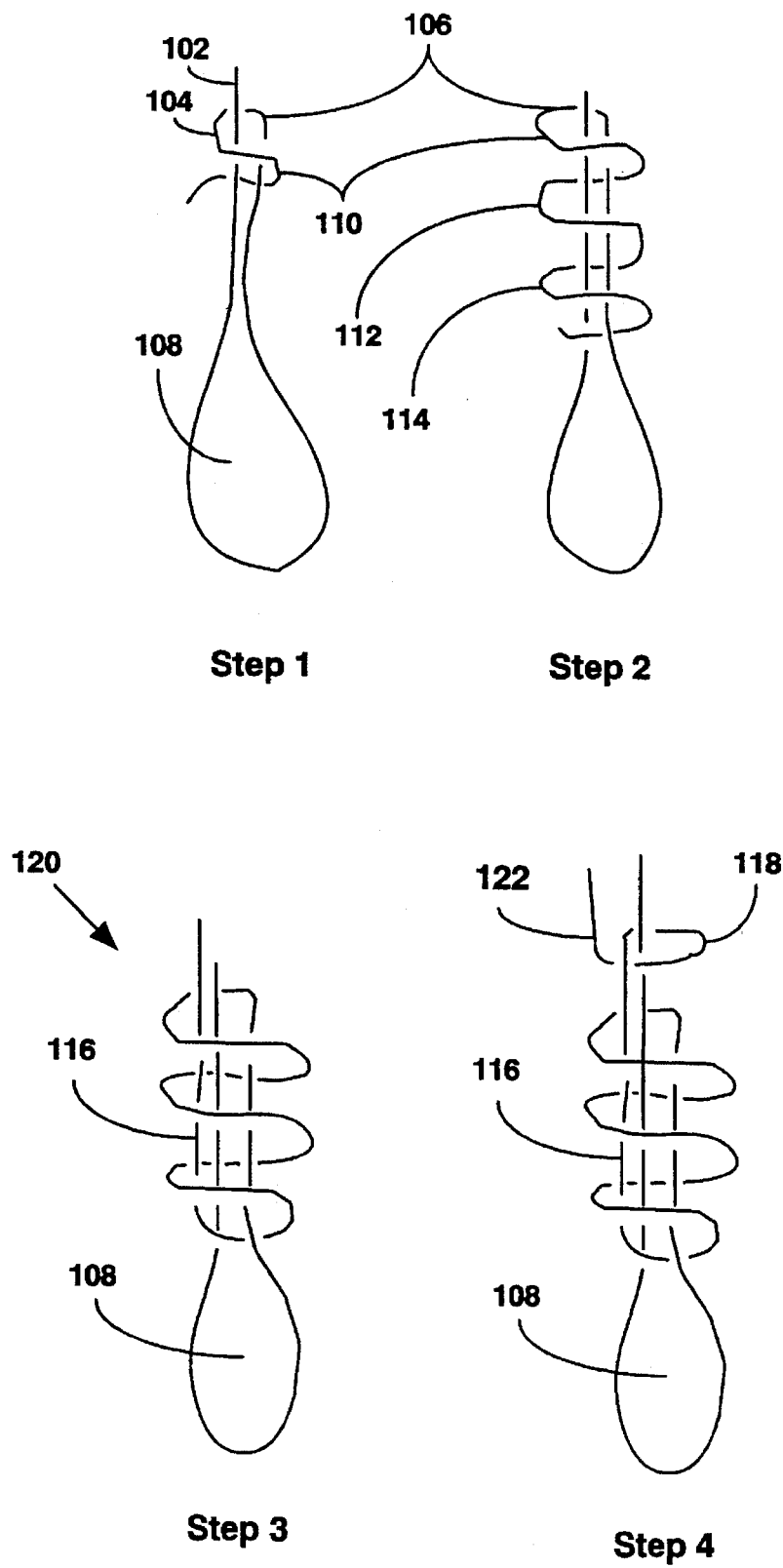
FIG. 1 is a diagram showing the first Lehrer knot which is a two hitched locking simple slip knot.

For ease of discussion, the following terms will be used in this disclosure:

1—The "noose" is the loop formed by a sliding knot on a rope or suture, as in a lasso.

2—The "bight" is the loop formed when first crossing the suture strands.

3—The "standing part" is the suture strand that is continuous with the noose and can be mobilized through the sliding knot to control the size of the noose. The "standing part" comprises the noose and the portion of suture that extends past the sliding knot. The length of this later segment varies inversely with the size of the noose.

4—The "end portion" is the suture strand that forms the loops and hitch/s that constitute the knot itself. Once the loops are tightened to form the knot, the length of the "end portion" remains constant and does not depend on the size of the noose.

5—The term "suture ligature" is a ligature made from suitable suture material which is passed through the tissue with a needle.

6—The term "loop ligature" is a ligature made from suitable suture material which surrounds the target tissue but does not pass through it.

7—The terms "suture applier" and "ligator device" will be used interchangeably herein.

For ease of illustration, the term peritoneal cavity is used when discussing the location of the surgery. However, any body cavity may be operated on using these techniques. Therefore, the term body cavity, peritoneal cavity, thorasic cavity, etc will be used interchangeably.

Prior to discussion of the suture applier, a disclosure of the following five new knots designed for use with the suture applier that is introduced will be made. The first, second, third, and fourth Lehrer Locking Slip Knots, followed by the Lehrer Double Noose Slip Knot. Those skilled in the art will recognize that while the knotting techniques disclosed herein enhance the surgeon's ability to apply ligatures and maximize the effectiveness of the suture applier, prior art knots with lengthened suture strands may also be used effectively with suture applier that is introduced. A preliminary explanation of how the knots are tied follows.

The five new knots are four locking simple slip knots and a double noosed non-locking slip knot. If the first Lehrer knot is used without its step 4, the resulting slip knot is non-locking. The first Lehrer knot is a double hitched simple locking slip knot. Its two suture strands are surrounded by the three loops that form the knot. One hitch is formed as the end portion enters the loops crossing under the anterior arch of the third loop and over the posterior arch of the second loop. The other hitch is formed after the end portion leaves the loops and forms a fourth loop around the standing part in a reverse direction to then cross the posterior arch of that fourth loop. This allows to transfer the bight to the standing part when tension is applied to the end portion suture to lock the knot. The slipping strength of this knot is superior to the prior art knots, partly due to the design of the knot and partly because these prior art knots cannot be effectively locked due to their design with a shortened suture end portion. The three new locking knots that follow are a variation of this knot.

In contrast to the first Lehrer knot, in the other Lehrer locking slip knots the end portion is surrounded by only two of the loops, as the end portion bypasses either the first, the second or the third loop, respectively. There is no difference in slipping strength between these three locking knots, as long as the surgeon places the bypassed loop distally, at the point where the standing part leaves the knot. The bypassed loop forms a second extra hitch that creates a bight on the standing part and will lock the knot, as long as it is positioned at the distal point of the knot. A third hitch may then be placed on the end portion and like the first Lehrer knot will be transferred to the standing part when pulling the end portion of the suture against the knot. All these triple hitched knots disclosed herein are securely lockable. The three hitched knots are best used on loop ligatures or on the pretied knot suture ligatures that complete the knot extracorporeally. The non-locking slip knot that features a double noose is formed over a double bight in a similar fashion as the first Lehrer knot. Of course, as with other slip knots, locking the slip knot with an additional extracorporeal knot takes little extra time, but provides the surgeon an additional margin of safety.

FIG. 1 shows the first Lehrer knot. This is a simple locking slip knot 120 tied using the end portion strand. While the preferred embodiment envisions three loops, those skilled in the art will recognize that more loops may be added. Likewise, extra loops may be added to any of the other knots discussed below.

In step 1, end portion 104 crosses under standing part 102 and is wound one time around bight 108, in a counterclockwise direction.

In step 2, end portion 104 is additionally wound one and one half times around the bight 108 in a manner similar to the first round turn, and enters bight 108 from behind. The third round is counted as only one half of a round turn, because its posterior arch is not completed as end portion 104 enters bight 108 before crossing standing part 102.

In step 3, the first Lehrer locking slip knot 120 is formed by drawing the end portion 104 under the anterior arch of all L5 three loops 110, 112, 114. A hitch 116 is formed as end portion 104 crosses under anterior arch of the third loop 114 and over the posterior arch of the second loop 112.

In step 4, another loop 118 is made with the end portion around the standing part, winding it in an opposite direction. Hitch 122 is formed as end portion crosses under the posterior arch of loop 118. The two ligature strands of slip knot 120 are enclosed by the three loops 110, 112, 114 that form slip knot 120, producing its superior slipping strength in comparison to other slip knots such as the Roeder loop and the Duncan loop.

Figure 2:
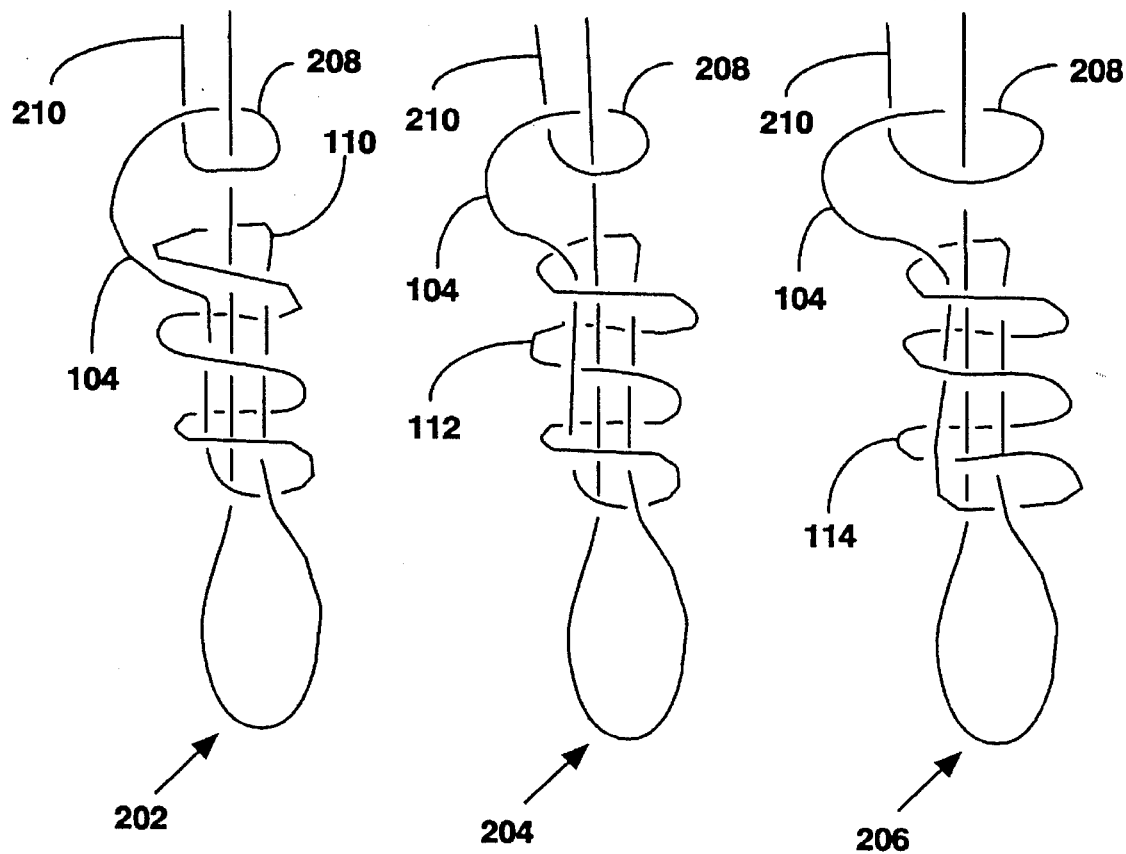
FIG. 2 which is a diagram showing the second, third, and fourth Lehrer knots which are triple hitched locking simple slip knots.

The three new locking knots 202, 204, 206 that follow are a variation of the first Lehrer knot 120. FIG. 2 shows how these knots may be fashioned using the end portion suture.

The second Lehrer knot 202 is made by drawing the end portion 104 under the anterior arc of the third loop 114 and the second loop 112, bypassing the first loop 110.

The bypassed loop forms a second hitch which may produce a bight on the standing part 102 when the knot is firmly tightened, locking it.

To make the third Lehrer knot 204, the second loop 112 is bypassed by the end portion 104 and it is brought to the distal part of the knot to be tightened where the standing part exits the knot.

In the fourth Lehrer knot 206, the third loop 114 is bypassed by the end portion 104, and likewise, it is brought for tightening to the distal part of the knot where the standing part exits.

The loop that is left only around the standing part should be placed at the point where the standing part exits the knot and loosely tightened after the other two loops are tightened first, taking care not to accidentally lock the knot.

In the knots described above, the third hitch 210 is produced by making another loop 208 with the end portion by which is wrapped around the standing part. The hitch 210 is formed as the end portion crosses under the posterior arch of the fourth loop. The third hitch 210 provides a superior degree of security of the first throw of the ligature because of the added bight it produces on the standing part, which effectively locks the knot. The first hitch formed by the first two loops must be tightened first as opposed to the second and third hitches which should be loosely formed and should be tightened with the end portion after the noose has been snugly applied to the tissues, as the final step in tying the ligature.

Figure 3:
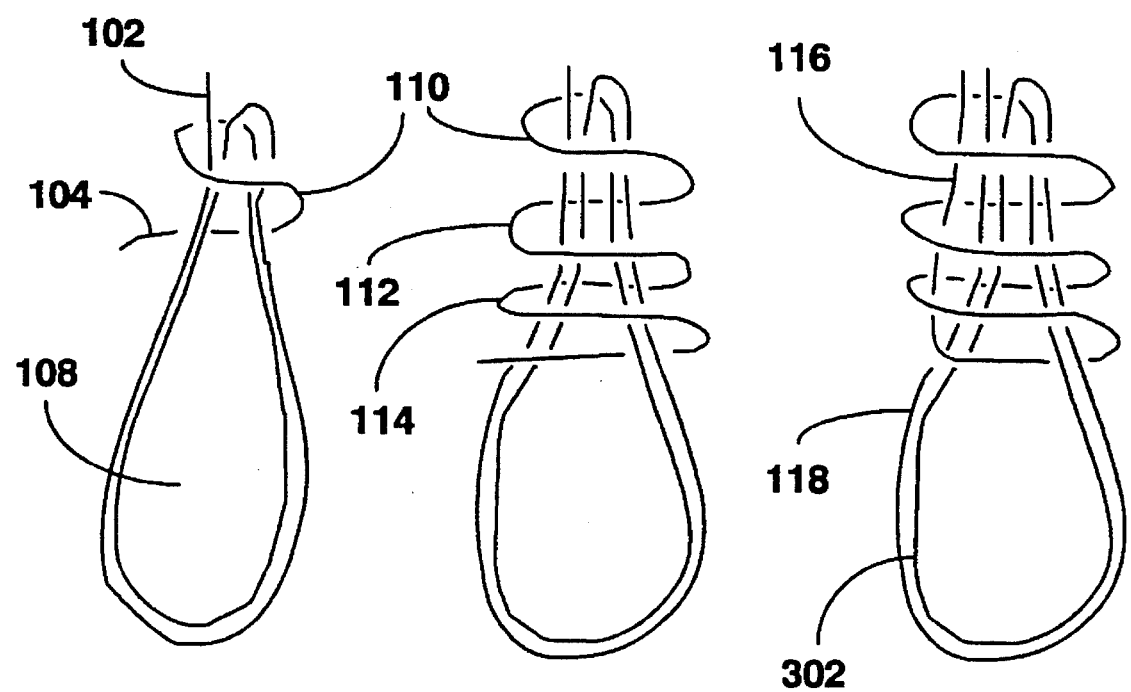
FIG. 3 is a diagram showing a double noosed slip knot which is a single hitched non-locking slip knot.

FIG. 3 shows the fifth Lehrer knot 302. The double noosed slip knot is formed over a double bight in a similar fashion as the first Lehrer knot.

The feature that is common to these five new knots is that the end portion 104 first crosses under the standing part 102 to then make two and one half turns around the bight 108 and enter bight 108 from behind, forming a hitch. The third round is counted as only one half of a round turn, because its posterior arch is not completed as the end portion 104 enters the bight 108 before crossing the standing part 102.

In the first Lehrer knot 120, the two ligature strands are surrounded by the three loops that form the knot.

In contrast, in the three locking slip knots 202, 204, 206 the end portion 104 is surrounded by only two of the loops, as it bypasses either the first 110, the second 112 or the third 114 loop, respectively. Those skilled in the art will recognize that while the procedure for fashioning the knots was disclosed from the point of view of using the end portion 104, the standing part 102 can also be used to make them as long as the resulting knot structure is the same and may be preferable depending on the preferences of the surgeon. Of course, pretied knots manufactured by machine will use whichever method is most efficient for the particular machine. As shown in the discussion of FIG. 18, below, the first Lehrer knot 120 can be fashioned using the standing part of the suture.

FIG. 18 shows an alternative method of fashioning the first Lehrer knot that is shown in FIG. 1 using the standing part rather than the end portion. This method can be used to fashion all the Lehrer knots with the exception of the fourth Lehrer knot. With this technique, the end portion makes three complete round turns around the bight without entering it. However, the basic structure of the knots formed with the standing part method is the same because the end portion enters the three loops which surround both suture strands and the hitches are the same on both methods.

As shown in steps 1 and 2, the standing part 1802 is crossed under the end portion 1804, makes three loops 1806, 1808, 1810 in a clockwise direction around end portion 1804, enclosing end portion 1804 within the loops 1806, 1808, 1810. In step 3, the third loop 1810 is drawn through the second loop 1806 and the first loop 1808; and through the bight 1812, forming the noose 1820. In step 4, another loop 1814 is made with the end portion 1804 around the standing part 1802 forming a second hitch 1818 in addition to hitch 1816 as it crosses under its posterior arch.

Once the locking slip knot has been formed, it is good practice to tag either the end portion 104 or the standing part 102 with a clamp to identify the suture strands. In the preferred embodiment, the standing part 102 is tagged, which helps supplement is lesser initial length.

The tying technique takes advantage of both ligature strands of the slip knot, which are left sufficiently long to span the distance between the target tissues and the outside. In the preferred embodiment of loop ligatures, the end portion 104 should be drawn about 30 centimeters (or about one third of the length of a 36 inch (90 cm) suture) out of the laparoscopic cannula (not shown), leaving outside the cannula about fifteen centimeters of standing part, to allow the extracorporeal manipulation of both suture strands after the slip knot has reached the target tissues. Those skilled in the art will recognize that while a 30 centimeter long end portion suture was used in the preferred embodiment, any suitable length of end portion suture may be used as long as there is adequate length for the surgeon to extracorporeally manipulate and/or tie ligatures.

In the preferred embodiment of pretied knot suture, the lengths of end portion 104 is similar to the loop ligature. However, the total length of suture is either 36, or preferably 48 inches.

The slip knot is loaded by its two ligature strands on suture applier 402 (shown below in reference to FIG. 4). The surgeon can manipulate separately each ligature strand from outside the abdominal cavity while holding the slip knot at the tip of suture applier 402.

Pulling standing part 102 through the knot itself effects the closure of noose 118 on the target tissues. In contrast to hitch knots, slip knots cannot be pushed because the loops of end portion sutures have been already tightened to form the knot. In fact, slip knots are held at the tip of ligator device 402 as standing part 102 glides through the knot itself while the surgeon gradually pulls it to effect the closure of noose 118. The position of the knot relative to the ligature strand is not necessarily related to the spacial positioning of the knot, which is held and positioned with the tip of suture applier 402. This concept will be presented in detail when discussing the preferred knot tying technique that may minimize trauma to the tissues.

The slipping strength of the slip knot is negatively affected when tension is applied to standing part 102. As discussed above, Hay correlated the increase in slippage rate of the knot with the number of pulls applied on the standing part. The tying of the slip knot of either loop or suture ligatures should be concluded with a final pull on end portion 104 while keeping the knot applied against the tissues with the ligator. The application of tension on end portion 104 is preferably deferred until after the noose has been snugly applied on the tissues, to prevent the knot getting accidentally jammed or even locked. The extracorporeal technique introduced herein allows the surgeon to easily restore the slipping strength of the knot by applying tension on the lengthened end portion 104, against the knot being held at the tip of a suture applier 402. This tightens the knot, increasing its slipping strength, and in addition, this may close the second and third hitches of the knot, forming one or two bights on the standing part that lock the knot. This technique can be effectively used to apply any of the self-locking slip knots presented herein. The above also applies to prior art slip knots to substantially enhance the slippage power.

When using one of the spools introduced herein for a pretied knot suture, leaving both suture strands long allows manipulation of the suture strands from the outside after bringing the standing part outside with a wire guide loop. Then by manipulating the end portion suture from the outside, the pretied loops can be pushed over an appropriate length of the standing part, thus completing the formation of a knot within the abdominal cavity, forming a small noose that may be tightened with a negligible sawing effect on the tissues.

The extracorporeal technique to make one or more extracorporeal hitch knots to further secure the slip knot is best accomplished if:

First, both strands of the suture are sufficiently long to make the extracorporeal knot. In the preferred embodiment of a loop ligature, sutures having lengths of 27 inches (67.5 cm) or 36 inches (90 cm) have been found to be suitable. The slip knot is located near the mid-point of a 27-inch (67.5 cm), or preferably, a 36-inch (90 cm) suture, which will leave an end portion that is about 13 inches (32 cm) long, as an approximate minimum length of end portion suture. After tying the slip knot, the standing part will have a similar length. Those skilled in the art will recognize that many factors, including the physical size of the patient, and/or the location of the laparoscopic port relative to the target tissues will influence the ideal length of a suture. Therefore, the only requirement as to suture length is that the strands be long enough to allow convenient extracorporeal knot tying. In the preferred embodiment of pretied suture, the end portion of the suture is about 30 cm long or 12 inches, and the total suture length is 36 or 48 inches.

Second, the hitch knot is made using the standing part of the slip knot.

Third, the hitch knot is loaded on the knot pusher instrument by the standing part.

If the end portion is instead used in any of the last two aforementioned steps, the tie may remain unlocked, which is important if the surgeon relies on just one security knot to lock the slip knot. However, when multiple security knots are used in sequence, bights can be transferred from strand to strand by alternatively reversing the relative direction before applying tension on the strands to tie each of the knots. This technique allows locking of the tie without switching suture strands when making the hitch knots.

In addition to the slipping strength provided by the knots themselves, the suture materials are also an important factor in the slipping strength of a slip knot. Catgut gives the highest slipping strength but is a poor choice because it is a highly reactive material. Braided sutures such as POLYGLACTIN (Vicryl or Dexon), and silk, have the second highest slipping strength; followed, in decreasing order, by POLYDIOXANONE (PDS), POLIGLECAPRONE (Monocryl), PTFE (Gore-Tex), POLYGLYCONATE (Maxon) and nylon, all of which are commonly available products.

When both the suture material and the slip knot have a low slipping strength, the effect of their combined use on the quality of the tie can be substantial. For example, the Roeder loop and, to a lesser extent the Duncan loop, have substantially less slipping strength when made with braided suture materials instead of catgut.

Locking knots such as the second, third, and fourth Lehrer knots, and the Weston knot (the Weston knot is well known in the art) have the best slipping strength, followed in decreasing order by the first and the fifth Lehrer knots, the Duncan loop and the Roeder loop. The reason for this difference lies in the structure of the knots. The superior slipping strength of the triple hitched locking Lehrer knots shown in FIG. 2 is due to the second and/or third hitch distally formed around the standing part; and the fact that the other two loops that form the knot itself enclose the end portion, holding it in place.

The three loops that form the first Lehrer knot in FIG. 1 are wrapped around the end portion strand, compared to only one of the four loops of the Duncan loop and the Roeder loop. In addition, the second hitch produces a better bight on the standing part, because of its location at a point where the standing part exits the slip knot, accounting for their different slipping strength in spite of the fact that all these knots have two hitches. Another factor that determines the slipping strength of a slip knot is the technique used to apply it to the target tissues. Each time that the standing part is pulled to tie the noose of the slip knot, the resulting straightening of the standing part tends to eliminate its bight and unravel the knot itself. Particularly in the case of the Roeder loop, because it only has one of its loops surrounding the end portion of the suture. The loss of slipping strength of the Roeder loop that occurs in proportion to the number of pulls to apply it, reflects the loosening of the single loop that holds the end portion and the loss of compression and/or distortion in the traject of the standing part, rather than the weakening of the suture material that Hay suggested as the explanation.

The loss of slipping strength that occurs as a result of the above can be reversed by applying tension on the end portion, while holding the knot in position with the tip of the suture applier 402. For this reason, the application of a loop ligature should conclude with a final pull on the end portion strand, to restore the knot itself, which is easily done with the extracorporeal technique and suture applier 402, discussed below.

As previously stated, making one or more extracorporeal security knots requires little time, and may provide an extra margin of safety. The surgeon should preferably use the standing part of the slip knot to fashion the security knot. In most circumstances, either the second, third or fourth set of Lehrer knots are sufficient with Vicryl/Dexon or silk; and only one extracorporeal security knot may be required with Gore-Tex, Maxon or nylon, provided that these knots are made and applied using the standing part of the slip knot.

The bulk of the knot is another relevant consideration. The Roeder loop and the Duncan loop have four round turns and therefore, are bulkier than the simple slip knots introduced herein, which have as few as two and one half round turns, but may have additional turns at the surgeon's discretion. The bulk of the double noosed slip knot is less than the corresponding bulk of two simple slip knots, because these two nooses share a single knot. While its bulk is larger than the bulk of any of the slip knots discussed herein, its bulk would fare favorably vis the combined bulk of three unlocked Roeder loop ligatures that the prior art applies on a single pedicle.

The Weston knot is a locking knot that is the smallest of all the knots compared. However, this is not an advantage from a technical viewpoint, because a knot of larger diameter is less likely to be pulled into the opening formed by the indented end of the suture applier 402 and the sheat 416 when tension is applied on the standing part to close the noose. In the Weston knot, the end portion forms only two loops around the two suture strands but its two long hitches tend to untwist after the Weston knot has been locked, when tension is applied distally on the noose. This causes the Weston knot to unbuckle, resulting in a slight loosening of the noose in spite of the fact that the knot is well locked. Once the Weston knot is locked, it may not be possible to again tighten the noose further. These observed effects are absent in the locking simple knots that are introduced herein, which have the additional advantages of being easier to make and place on the mid-portion of the suture; and of having considerable less tendency to get accidentally locked. The Weston knot can be loaded on the suture applier 402 by both suture strands, which is the technique that works best for all locking slip knots.

Figure 4:
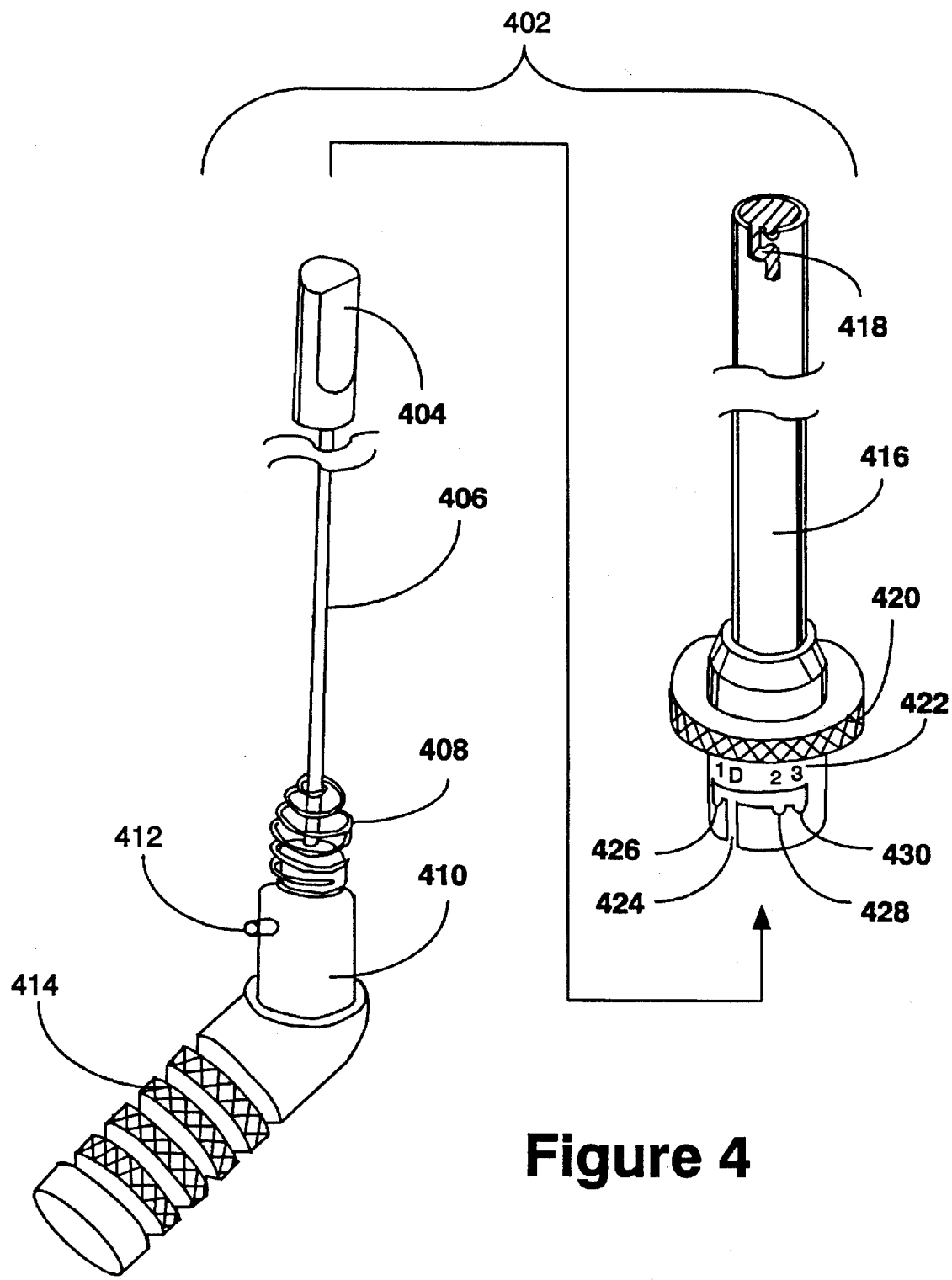
FIG. 4 is a diagram of a preferred embodiment of the ligator device.

Turning now from the knots to the apparatus for applying the sutures, FIG. 4 shows the preferred embodiment for the invention in non-disposable form. In this embodiment, as well as the others discussed below, the foregoing knots are manipulated by the particular suture appliers such that they can be held and tied at the distal end of the applier in close proximity to the target tissue, by manipulating the suture strands extracorporeally. The preferred embodiment envisions a distal opening and a distal side opening. The distal opening is intended to keep the knot of the slip knot at the tip of the ligator such that it is not dragged into the space between the indented surface of the shaft and the sheat when tension is applied to the sutures. The distal side opening through which the sutures exit the instrument is intended to easily open for accepting the sutures into the instrument and to enclose or fixedly grasp the sutures at the point where they exit the instrument so that they can be manipulated externally against the knot that is held at the tip of the instrument. For ease of illustration, lengths of the instruments, and their corresponding widths are not drawn to scale in order to more readily show the particular features of the mechanical structures in question. In practice, as with other endoscopic suturing instruments the usable length of shaft is about 30 cm which is enough for the surgeon to conveniently reach the target tissues in a patient. Likewise, the diameter of the instrument at the distal end has to be wide enough to fit through the size access port selected by the surgeon. In the preferred embodiment, it should be able to fit through a size 5 laparoscopic cannula and accommodate the particular type of suture and/or guidewire being used. Of course, the proximal end should be of a size to allow the surgeon to conveniently manipulate it by hand. In this embodiment, suture applier 402 is made of a tubular external sheat 416, and a solid shaft 406, that forms one body with the handle 414.

Sheat 416 and the shaft 406 are sized to fit telescopically one within the other. They are held together by the retainer 412 of shaft 406, which is maintained in place within one of the three notches 426, 428, 430 of sheat 416 under pressure from spring 408. One end of spring 408 rests against the widened proximal end 410 of shaft 406. The other end of spring 408 fits within the widened proximal end 422 of sheat 416 and provides outward pressure to hold retainer 412 in whichever notch 426, 428, or 430 which is selected. Shaft 406 is initially inserted into sheat 416 such that retainer 412 slides into opening 424. When retainer 412 is fully inserted, sheat 416 is rotated to one of the notches 426, 428, or 430. Retainer 412 and notches 426, 428, and 430 are in alignment with their corresponding distal slot 418. Suture applier 402 has three settings—Open, Enclose and Fasten—that are selected by rotating the retainer into one of the three notches 426, 428, or 430, respectively of sheat 416.

To operate suture applier 402, sheat 416 can be axially rotated using a single hand gripping intermediate portion 420, while holding suture applier 402 by handle 414. The surgeon first pulls sheat 416 toward handle 414 to compress spring 408, disengage retainer 412, and coaxially rotate sheat 416 over shaft 406. This rotation results in distal opening of slot 418 moving in and out of alignment with the indented surface 404 of suture applier 402, depending on which one of the three notches 426, 428, or 430 of sheat 416 retainer 412 is placed. For ease of illustration, the width of shaft 406 is shown greatly enlarged at the distal end to provide a better view of indented surface 404.

FIG. 5 shows the three positions A, B, and C (open, enclosed, and fastened) of the distal end of suture applier 402 when the three notches 426, 428, and 430 are engaged. In the open position A, retainer 412 is placed within first notch 426, the indented surface 404 of suture applier 402 and the distal opening of distal slot 418 are in alignment, allowing suture applier 402 to easily admit one or two suture threads within the opening formed between indented surface 404 and sheat 416.

In the enclose setting B, the distal opening of distal slot 418 is closed by the underlying shaft, thus loosely enclosing the suture within the proximal section of distal slot 418 that remains open on the side of the instrument. Enclosed position B is engaged as follows. Sheat 416 is rotated, moving retainer 412 into notch 428. This places distal slot 418 of suture applier 402 out of alignment with indented surface 404. This prevents the suture from falling out of suture applier 402. However, because distal slot 418 has two parallel sections, one distal and the other proximal, the proximal section remains in alignment with indented surface 404 while the distal section is no longer in alignment. This allows the suture to freely slide within suture applier 402 without disengaging from suture applier 402. In the enclose setting B, suture applier 402 can be used to apply and tighten the slip knot of suture and loop ligatures. In addition, it can be used as a closed-end knot pusher, to deliver one or more extracorporeal security knots to lock a tie, like in Open Surgery. A Surgeon's Knot and/or one or more hitch knots can be applied without encountering the loss of contact with the suture that can occur with the prior art open knot pusher devices.

Further rotation of sheat 416 places retainer 412 into the last notch 430 (fasten position C). Distal slot 418 is almost completely obliterated by the underlying shaft, resulting in the fastening or gripping of the suture—or sutures—that were loaded on suture applier 402. In this position, the side opening of distal slot 418 is substantially closed such that a suture is firmly grasped by suture applier 402. Those skilled in the art will recognize that the size of the lateral enclosure can be adjusted to fit a variety of suture materials. Likewise, the indented surface 404 can be made of various widths or can be shaped as a groove, which determines the size of the distal opening of the space formed between the shaft 406 and the sheat 416 by the indented surface 404, in order to fit a variety of slip knot sizes and prevent the knot from being drawn into the space formed between the indented surface 404 and sheat 416 when tension is applied against it with the suture strands.

Suture applier 402 can be used in the fasten setting to introduce loop ligatures into the peritoneal cavity. The slip knot is preferably loaded by both suture strands and it is positioned centrally on the tip of suture applier 402 to be inserted through a laparoscopic cannula. This may require an introducer tube, unless a trapless cannula is used.

This setting can also be used to introduce or remove suture needles through a laparoscopic cannula, by grabbing the suture at one or two-centimeter distance from the needle.

In the preferred embodiment, the suture applier 402 fits through a size #5 laparoscopic cannula, leaving extra room for the sutures. However, those skilled in the art will recognize that the size of suture applier 402 can vary to suit the needs of a particular procedure. Likewise, the number of notches can also be varied. For example, four, five, or more notches could be employed to allow suture applier 402 to hold a variety of suture thickness sizes. In addition, only two notches may be employed to create a device which has only open and enclose positions with no fasten position, and functions as a closed end knot pusher.

Figure 6:
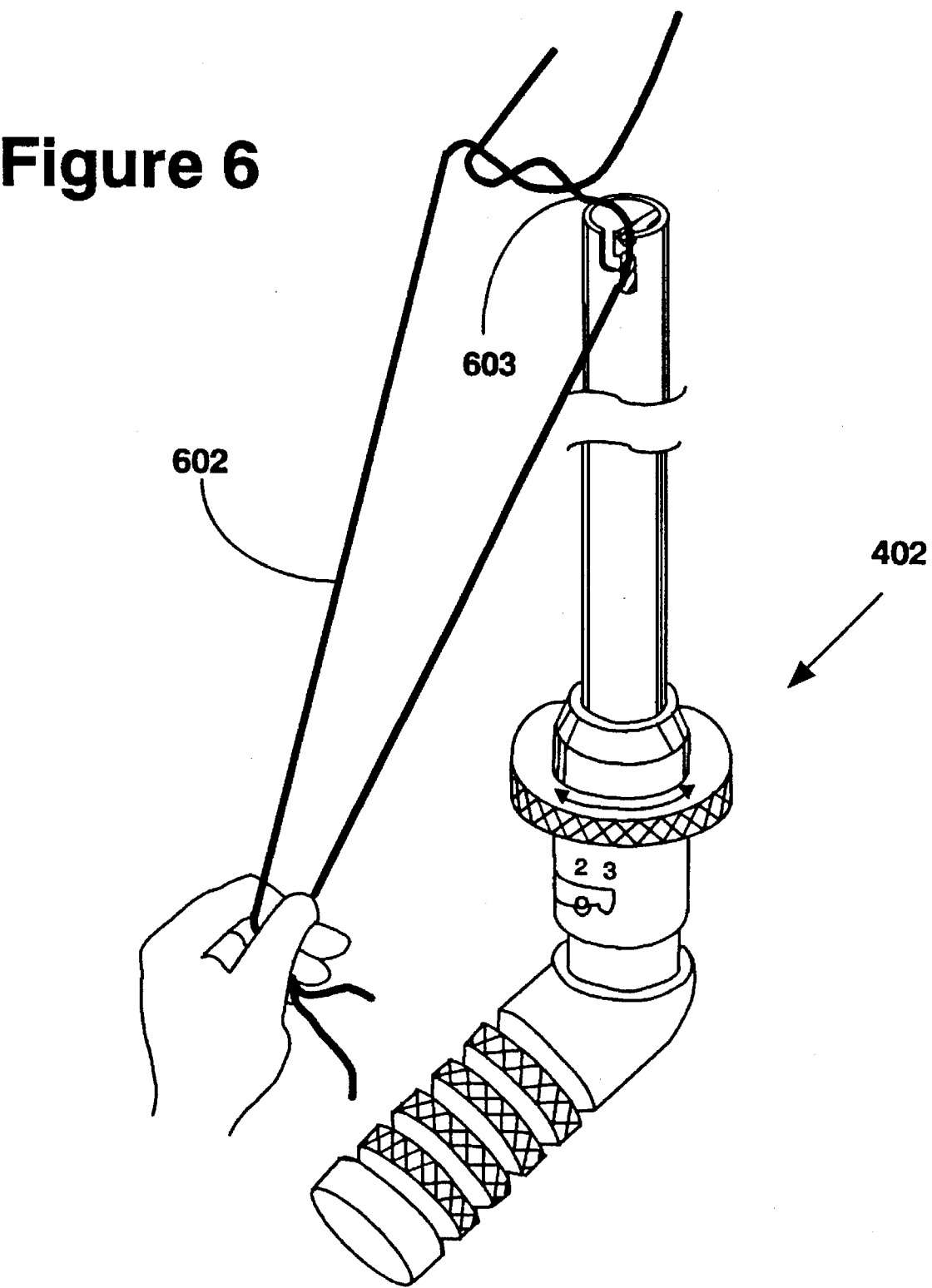
FIG. 6 shows the ligator device of FIG. 4 in use as a knot pusher.

In FIG. 6, the standing part 603 of previously tied suture slip knot is shown loaded onto suture applier 402 in enclose setting B. This allows the surgeon to extracorporeally push a hitch knot and tie it on the tissues without the problem of losing control of the suture. This suture should be slightly longer than the end portion 602 of the suture that is proximal to the hitch knot in order to facilitate pushing the knot toward the tissues.

The ease of loading this instrument makes it suitable for use as a reusable ligator apparatus in conjunction with ready made slip knots for loop ligatures, or pretied knot sutures mounted on a spool. This also effectively opens the doors for surgeons to make their own loop ligatures and suture ligatures using regular suture materials. As mentioned before, the instrument can also be used as a knot pusher that is easy to load, which allows surgeons to extracorporeally make an effective square tie with a minimum number of knots by alternately switching the suture strands as in open surgery when forming each of the hitch knots, which is an advantage in comparison to other closed-end knot pusher devices because the surgeon is more assured of delivering a square tie.

Figure 7:
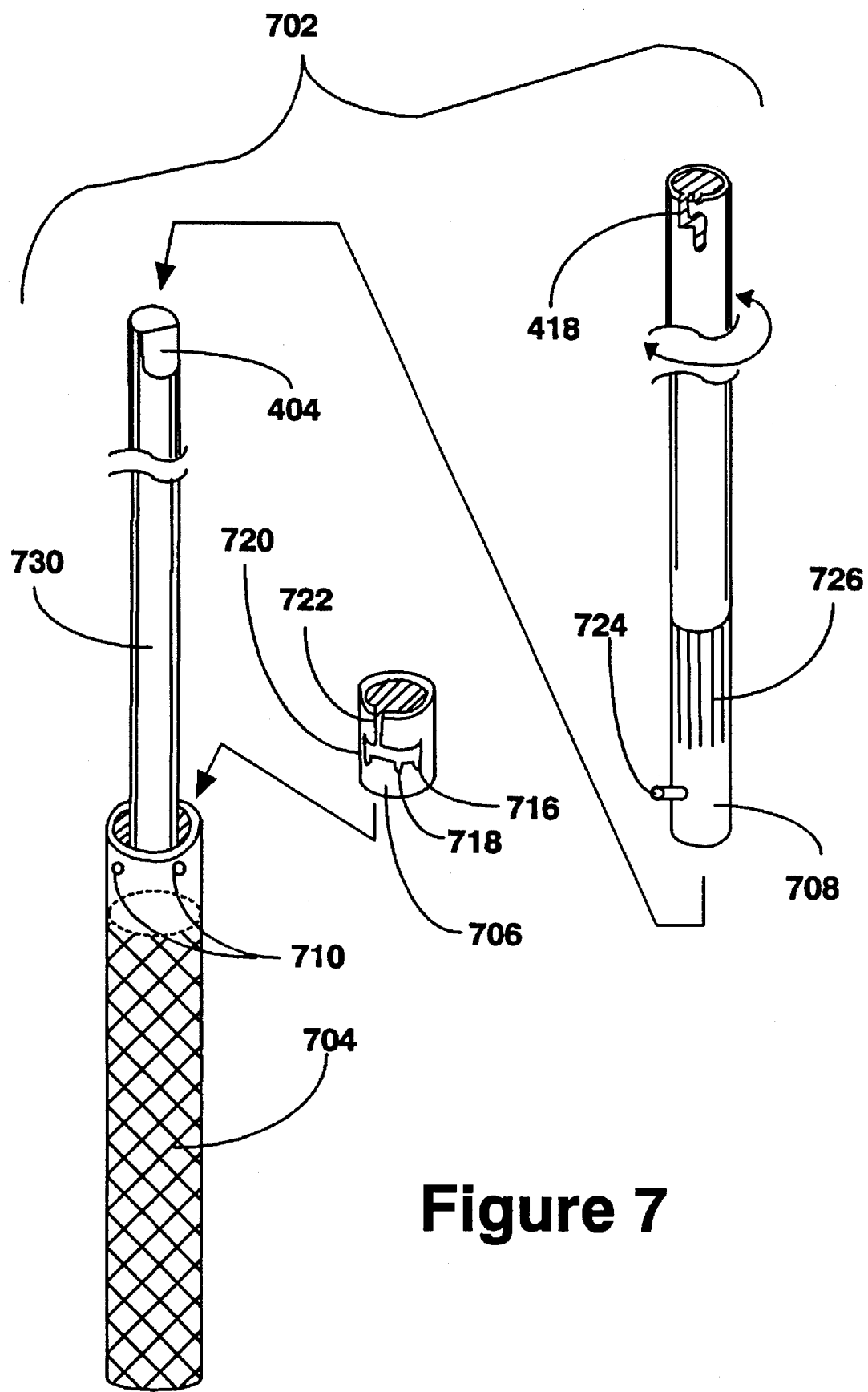
FIG. 7 is an exploded view of an alternative embodiment of the ligator device.

An alternative embodiment in the form of a disposable suture applier 702 is illustrated on FIG. 7. Similar to the reusable suture applier 402, the surgeon places the two components of the instrument in or out of alignment by rotating sheat 708 over shaft 730 while holding handle 704. Only the proximal portion of disposable suture applier 702 was changed from the design discussed above in relation to FIG. 4, leaving the same distal elements on sheat 708 and on shaft 730.

Sheat 708 is greatly simplified by eliminating intermediate portion 420 and spring 408. Intermediate portion 420 is effectively replaced by providing a knurled surface 726 for gripping. Spring 408 is replaced by providing a pressure fit created by constructing slot insert 706 of flexible material such as plastic or the like. This allows slot insert 706 to either deform when sheat 708 is inserted into slot insert 706 and retainer 724 is then rotated into one of the notches 716, 718, or 720, or it allows retainer 724 to snap in and out of notches 716, 718, or 720 on the proximal end of the shaft.

The wider segment 410 of shaft 406 was likewise eliminated and retainer 724 was transferred to the outside of sheat 708.

In the preferred embodiment, the distal portion of handle 704 is tubular and extends about 1.5 to 2 centimeters over the end of the shaft, which forms one body with it, as in the reusable suture applier 402. Those skilled in the art will recognize that this distance is not critical and may be modified to suit variations in design.

Slot insert 706 has an L-shaped slot and three notches. It is attached inside the tubular portion of handle 704. Slot insert 706 is held in place by set screws 710. Those skilled in the art will recognize that any suitable retention means may be used in place of set screws 710, such as rivets, tacks, glue, epoxy, etc.. However, screws allow the operator the versatility of rotating slot insert 706 to fine tune the instrument by realigning the notches.

Sheat 708 is sized to telescopically fit within handle 704 and around shaft 730. Sheat 708 has a knurled portion 726 that is ergonomically placed close to handle 704 of suture applier 702 and may be placed across the surgeon's index finger to grasp it between the index and thumb fingers. The retainer snaps in or out notches 716, 718, 720 when the surgeon pulls or pushes sheat 708 to rotate it and operate the device.

Figure 8A:
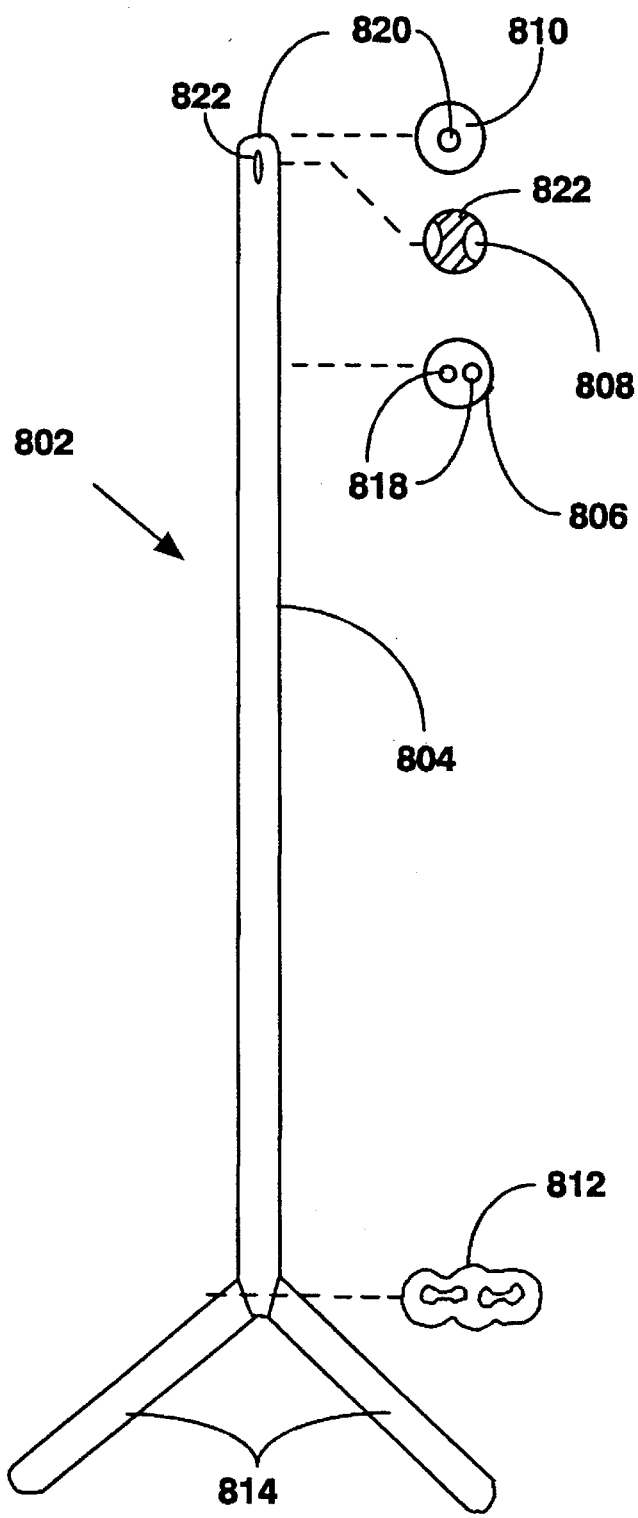
FIGS. 8A–8C are the third embodiment of the ligator device.
Figure 8B:
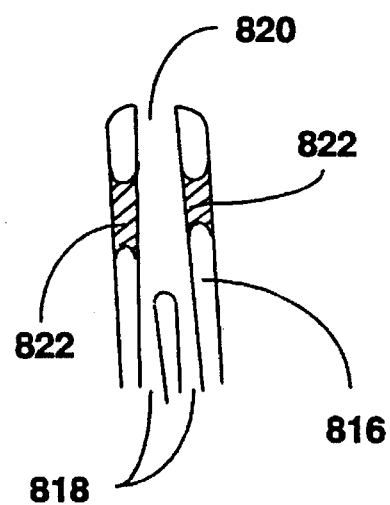
Figure 8C:
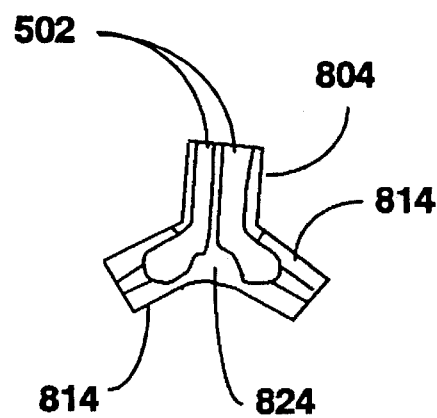

Another alternate embodiment of the suture applier 802 is illustrated in FIG. 8. This embodiment is a loop ligator that is designed to separately manipulate lengthened suture strands from outside the body cavity in order to effectively apply locking slip knots and further secure them with extracorporeal hitch knots. Cross sectional views A, B, and C illustrate the internal structure of the suture applier 802. Its shaft 804 has dual channels 818 that each accommodate a suture strand (not shown). The dual channels 818 are shown in the cross sectional views 806 and 816. Side openings 822 which connect to create a transverse channel (e.g., an interior space) are shown in a frontal view, in cross sectional view 808 and in cross sectional view B to illustrate how one of the suture strands of a hitch knot may be inserted into side opening 822 and then extracted through the other side opening 822. One of the side openings 822 is larger than the other to provide an oblique direction on the suture strand that is loaded through them when pushing a knot. This facilitates advancement of the knot through a narrow cannula. As shown in FIG. 6, the surgeon holds together the proximal part of the two suture strands on the left hand, leaving 2 or 3 centimeters longer the one that was loaded on the ligator. In addition, the tension on the sutures distal to the knot is released while the knot is being pushed in order to help the knot advancing and to avoid pulling the sutures of the tissues. This allows the instrument to be used as a closed end knot pusher when adding hitch knots to secure the tie. Cross sectional view 810 shows distal opening 820 at the distal end of suture applier 802. Cross sectional view 812 shows channels 818 at the entrance to breakable portions 814. The narrow width of the channel 818 in cross section 812 shows a method of taughtly holding the suture on the breakable portions. This allows suture applier 802 to be used as a loop ligator, which when loaded with one of the Lehrer locking knots effectively delivers a secure first tie. Using the same ligator as a knot pusher, this tie may be further secured with one or more extracorporeal knots. In the preferred embodiment, the shaft 804 is 27-cm long with two additional 3-cm long, separate breakable portions 814. Those skilled in the art will recognize that the lengths are not critical and may vary for convenience to suit a particular surgical procedure.

The slip knot (not shown) is kept centered on the tip of the suture applier 802 and its two suture strands 502 are threaded through a single distal opening 820 that does not accommodate the knot. The channels 818 diverge in shaft 804 at bulge 824. Separate breakable plastic portion 814 holds the ends of the sutures and is color coded to distinguish the end portion of the suture from the standing part. In the preferred embodiment, the portion holding the standing part is color coded green and the end portion is red. A 1 m slot 822 is made on each side at approximately 2 millimeters from the tip of the suture applier 802 to adapt it for use as a closed-end knot pusher to apply additional extracorporeal knots. A snare wire may be enclosed to help loading the suture strands.

A variety of suture materials and suture sizes could be used, from microsutures to larger suture materials. In the preferred embodiment, suture applier 802 comes with one of the previously described locking simple slip knots, or with the double noosed slip knot. The ready-made slip knot is placed on the mid-portion of a 36-inch suture.

The method used with suture applier models 402, 702, 902, 1002, and 1302 to hold the slip knot for insertion through the cannula is designed to prevent the noose from getting accidentally closed by the drag that the seal of the cannula produces on the knot itself and/or on its suture strands. That may have been one of the reasons to design the prior loop ligatures with a shortened end portion. However, the benefits of making a slip knot with a long end portion far outweigh the above potential drawback by allowing the effective use of self locking slip knots and of an easier extracorporeal technique for making additional security knots. A slip knot that has long suture strands may also be inserted through a cannula by the alternative method of grasping it with a suture grasper at the point where the end portion strand is the closest to the knot.

Instrument model 1702 requires an additional introducer tube to completely enclose the slip knot and the noose inside it before introducing it through the cannula. Further, suture appliers 402, 702, 802, 902, 1002, or 1302 can be used, as discussed earlier, to apply either a loop ligature or a suture ligature. In the later situation, the suture applier 402, 702, 802, 902, 1002, or 1302 is first used to tie the first throw of the suture, using an extracorporeal technique. The suture ligature is tied by manipulating the suture strands extracorporeally and using either one of the two needle through noose techniques to tie a suture ligature, forming a secondary noose. It can also be used with one of the two pretied knot suture techniques. In the needle through noose technique, the suture needle is first passed through the tissues and then through the noose of the slip knot, creating a secondary noose. The secondary noose is then locked with three or four extracorporeal hitch knots using the suture applier 402, 702, 802, 902, 1002, 1302 which is then used as a knot pusher. With this technique of suture ligature, the needle may be attached to the end portion strand or to the standing part. Two other techniques use one of the knots that have been pretied after the standing part with a needle attached to it has been drawn out of the loops of the slip knot. These techniques will be discussed more fully below in regard to FIGS. 14, 15 and 16.

Figure 9:
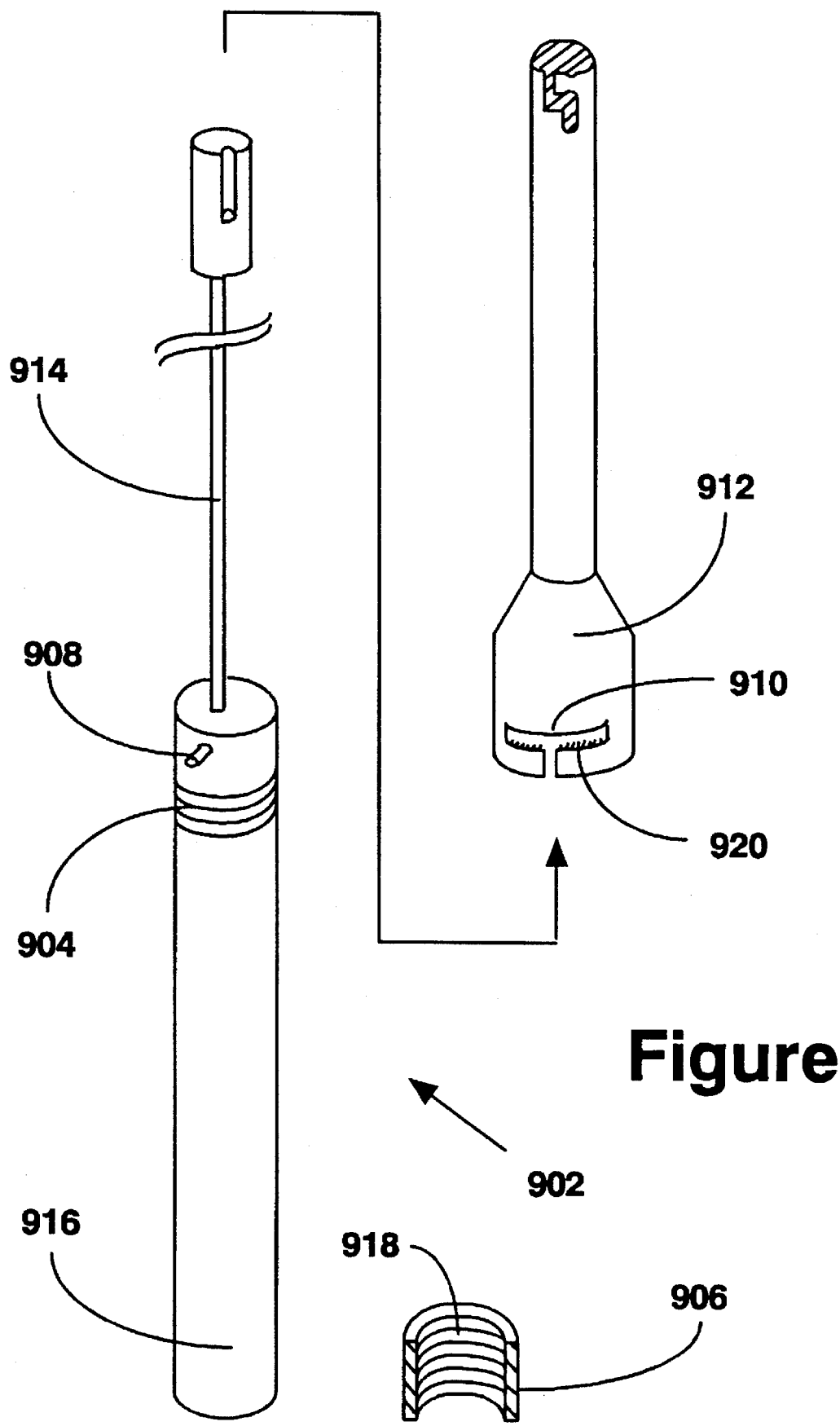
FIG. 9 is a fourth embodiment of the ligator device.

FIG. 9 shows another alternative embodiment. In this embodiment, sheat 912 is mounted on shaft 914. Retainer 908 (which is fixed to shaft 914 in the preferred embodiment) enters slot 910 and is held in place by means of a pressure nut 906 (shown in cross sectional view to expose the inner threads 918). The pressure nut fits over the proximal end of the handle and engages threads 904, pushing the proximal end of sheat 912 forward, compressing the retainer 908 against slot 910, thus holding the setting mode. In the preferred embodiment, the proximal edge of slot 910 is notched with many small serations 920 to accommodate a variety of positions without slippage of retainer 908 when it engages slot 910. This embodiment allows a variable number of positions to be set. By so doing, any size suture material may be grasped by a single suture applier. However, the distal opening between shaft 914 and sheat 912 must be adjusted to hold the knot outside the suture applier 902 by manufacturing devices that have indentations of various sizes at the distal end of shaft 914.

Figures 10, 10A:
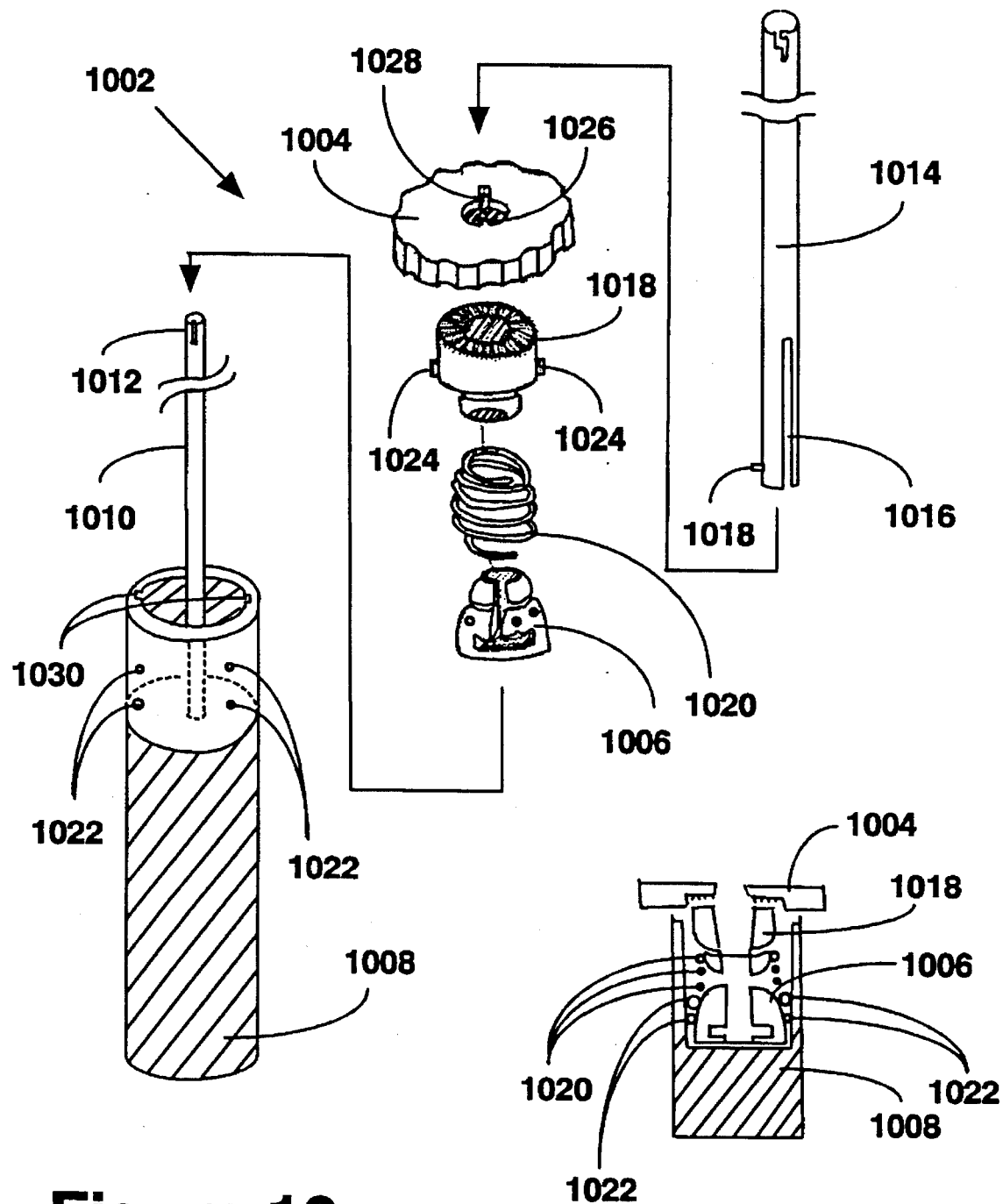
FIGS. 10–10A are fifth embodiments of the ligator device.

FIG. 10 illustrates a second embodiment which also allows a variable number of positions to be set on the distal end of the instrument. In this embodiment, slot insert 1006 is sized such that a portion of the internal space of handle 1008 is taken. The remaining portion is used by the clicker assembly 1018 and spring 1020. Wheel 1004 is positioned above handle 1008. Clicker assembly 1018 has teeth on the distal surface which fit into a recessed portion of wheel 1004 which has a corresponding set of teeth. Sheat 1014 is inserted through wheel 1004, clicker 1018, spring 1020, and slot insert 1006. Sheat 1014 is then mounted over shaft 1010 and its proximal retainer 1018 enters into slot insert 1006. Holders 1022 in turn hold slot insert 1006 in place. Holders 1022 may be screws, rivets, glue, or any other appropriate method of retaining slot insert 1006 in place. Clicker retainers 1024 fit into handle slots 1030 preventing its rotational movement while allowing it to move in a distal or proximal direction. Clicker 1018 is pressed against wheel 1004 by spring 1020. Wheel 1004 in turn is held in position by the key 1026 which fits into slot 1016 of sheat 1014 which in turn is held within the transverse portion of the slot of slot insert 1006 which is in turn fixedly attached to the handle 1008. When wheel 1004 is rotated, clicker 1018 is compressed against spring 1020 and snaps from tooth location to tooth location.

Insert A shows a cross sectional view of wheel 1004, clicker 1018, spring 1020, and slot insert 1006 as aligned in handle 1008.

Figure 11:
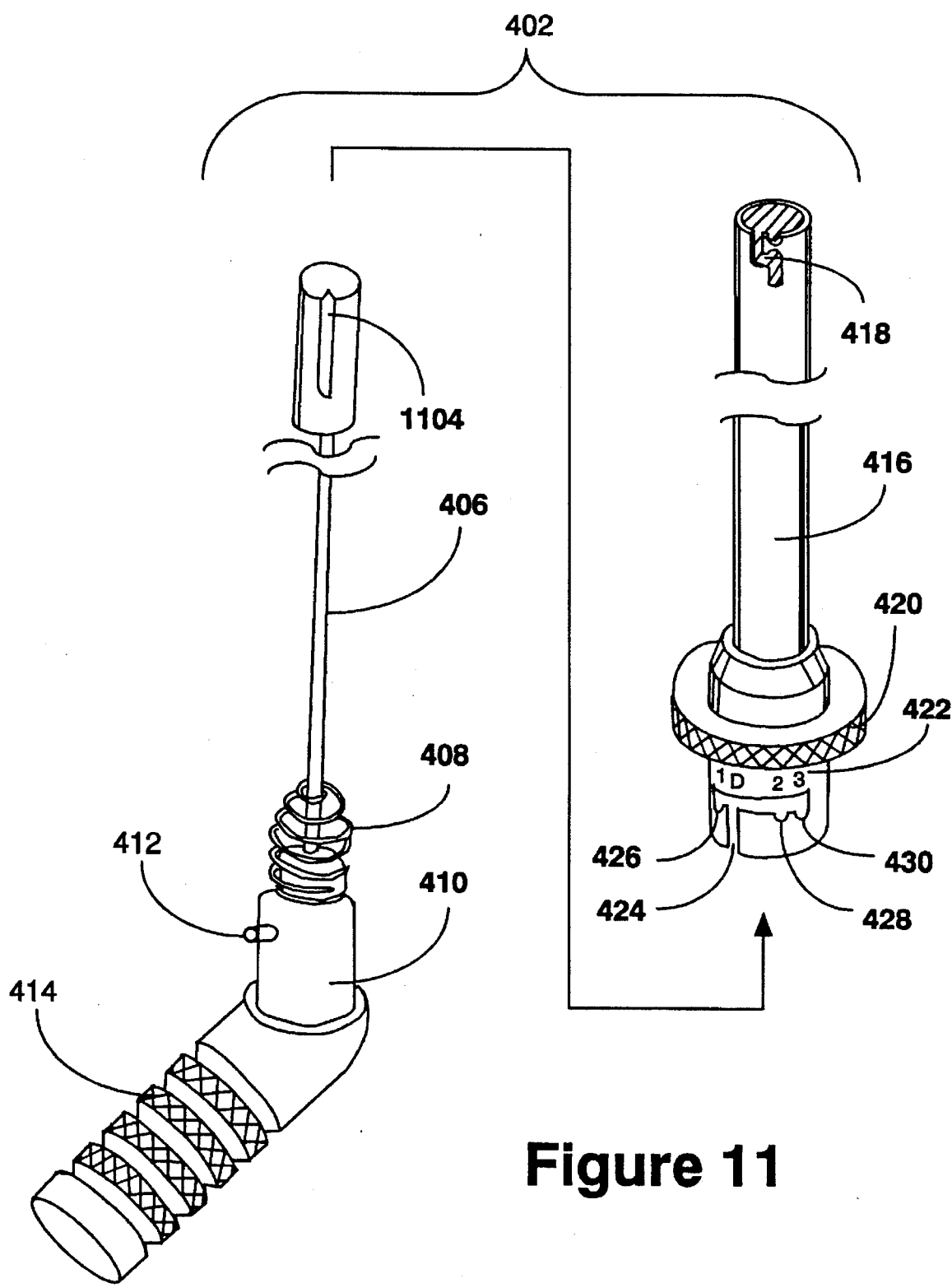
FIG. 11 is an alternative embodiment of the ligator device disclosed in FIG. 4.

FIG. 11 illustrates an alternative embodiment of the device shown in FIG. 4. In this embodiment, the indented surface 404 is replaced by distal groove 1104. Groove 1104 is discussed below in more detail in the discussion of FIG. 12.

Figure 12A:
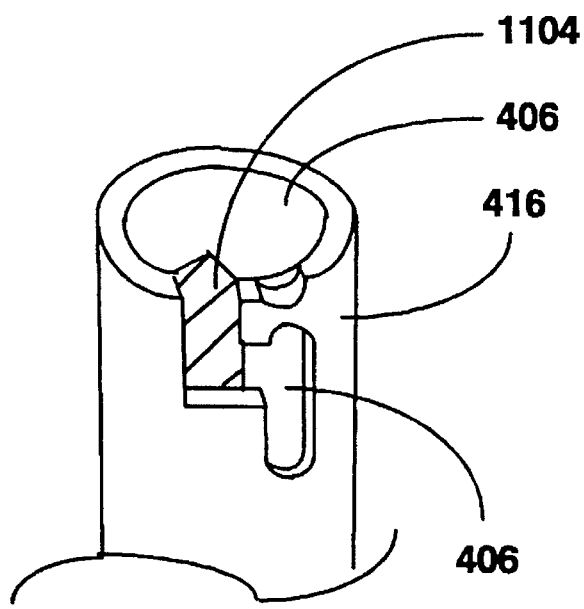
FIGS. 12A–12C are a detailed view of the distal end of the ligator device of FIG. 11.
Figure 12B:
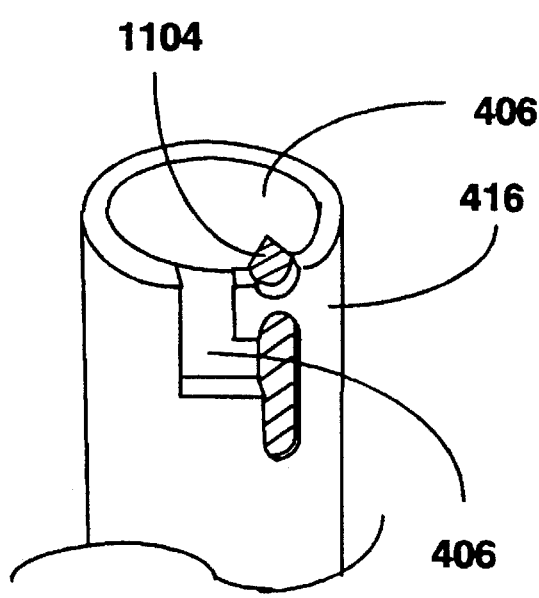
Figure 12C:
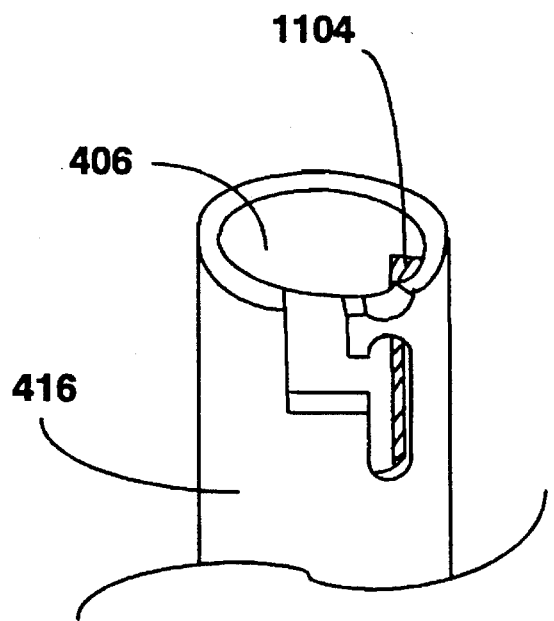

FIG. 12 is an enlarged view of the distal end of the device shown in FIG. 11. As can be seen when compared with FIG. 5, the groove 1104 provides a smaller area for a suture and reduces the possibility of a suture knot becoming lodged between the shaft 406 and the sheat 416, and allows smaller knots to be used.

Figure 13:
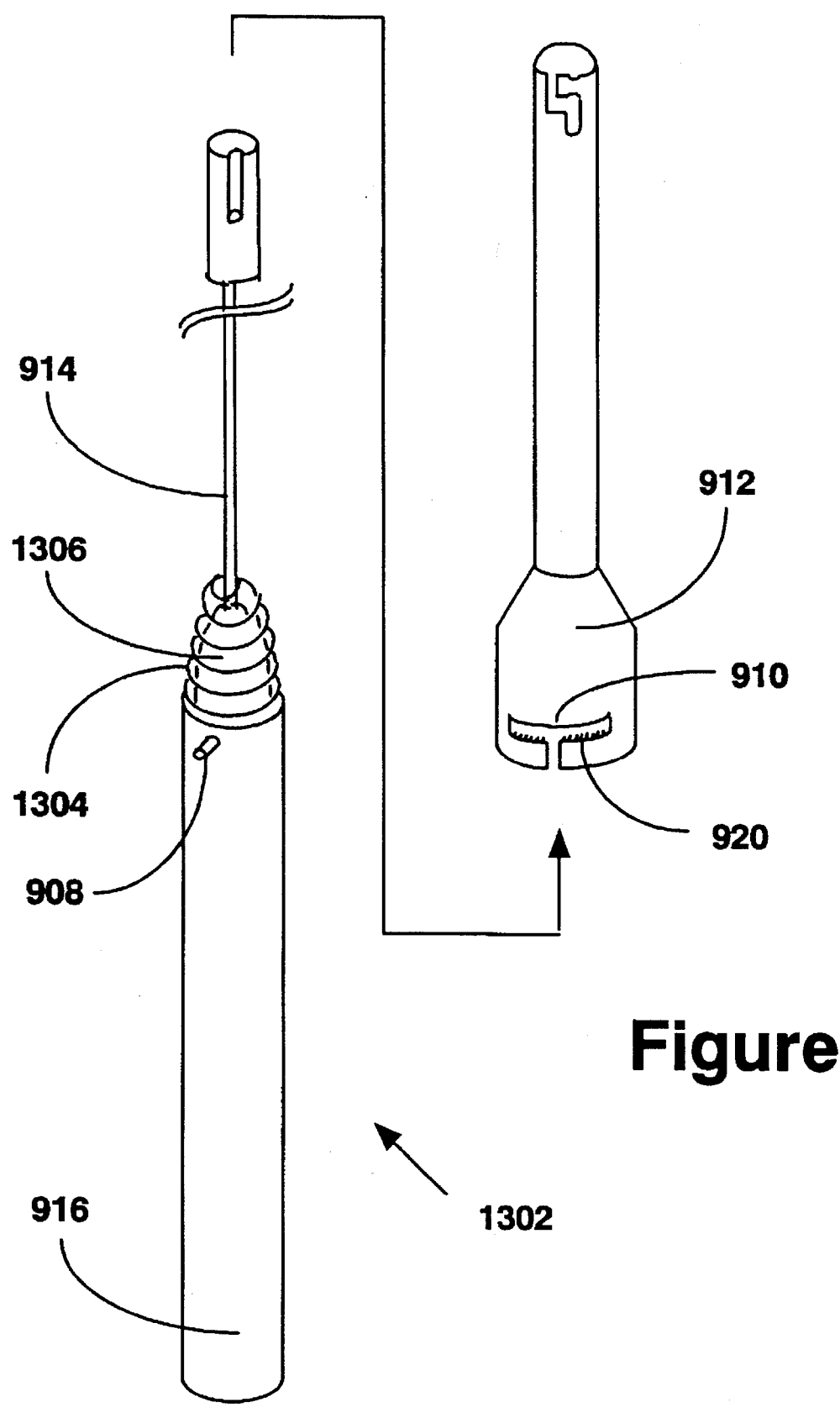
FIG. 13 is an alternative embodiment of the ligator device shown in FIG. 9.

FIG. 13 is an alternative embodiment of the ligator applier 902 discussed above in relation to FIG. 9. In this embodiment, pressure nut 906 and threads 904 are replaced by spring 1304 which mounts over widened base 1306.

Figure 14:
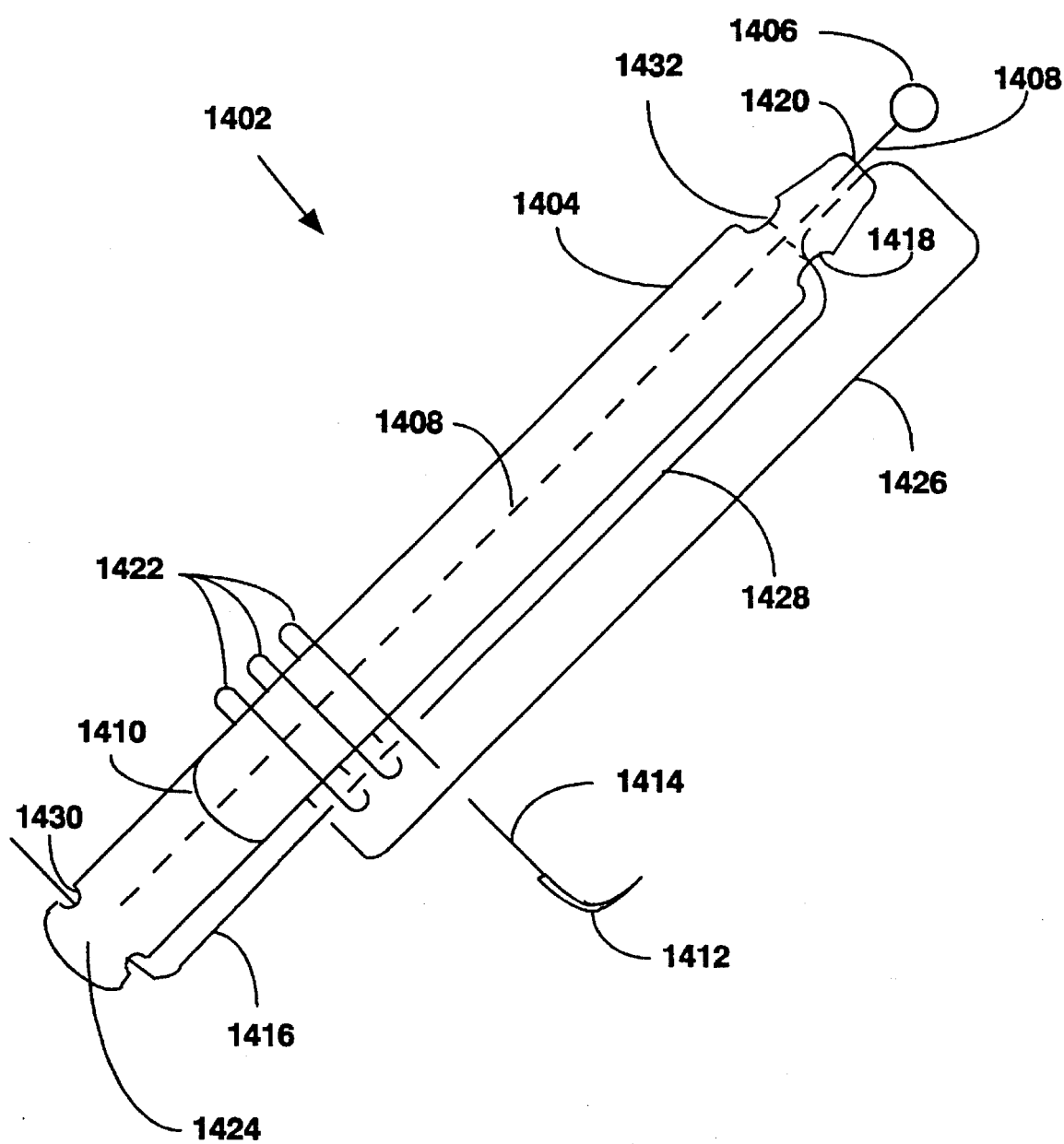
FIG. 14 is an alternative embodiment showing a pretied knot suture that comprises a disposable ligator applier with sutures mounted on its shaft. The pretied loops of the first Lehrer knot are shown. This knot having its step 4 omitted and the standing part suture pulled out of the loops of the knot.

FIG. 14 is a disposable embodiment of the ligator applier 1402. For ease of illustration, the diameter of shaft 1404 is shown greatly enlarged in relation to the length to better illustrate the structure of the device. Also, the suture which is comprised of end portion 1416 and standing part 1414 is shown with a relatively short length to eliminate clutter in FIG. 14.

Suture applier 1402 is used with a pretied knot suture that is designed to intracorporeally complete a slip knot that has a small noose and that might be tied without producing a significant sawing effect on the tissues. An initial discussion of suture applier 1402 as it is configured prior to use follows. The preferred knot is the first Lehrer knot which is fashioned as outlined above in the discussion of FIG. 1, preferably without the second hitch produced by step 4. The suture needle 1412 is attached to the standing part 1414 of the suture which is pulled through the knot 102, undoing the noose but leaving the pretied loops of the knot 1422.

The method to load these loops on the ligator instrument is as follows. The first step consists of introducing the end portion 1416 through the opening 1420 on the distal end of suture applier 1402, which has an interior channel of a size sufficient to accommodate both the end portion 1416 and guide wire 1408. Then the end portion 1416 exits through side opening 1418.

The second step consists of mounting pretied loops 1422 over the shaft 1404 loosely enough such that they may slide along the surface of shaft 1404. These pretied loops 1422 are placed proximal to the side opening 1418. This creates two external loops 1426 and 1428. These loops 1426, 1428 are part of the end portion of the suture. Loop 1426 extends from the third pretied loop to opening 1420 on the distal end of the ligator. Loop 1428 extends from side opening 1418 to the end of the end portion 1416 passing within the first two distal pretied loops. By pulling the loop 1426, the pretied loops can be loosened of the shaft 1404 and can be displaced toward the proximal end of the ligator dragging the end portion of the suture into the suture applier. Conversely, pulling the end portion of the suture 1416 mobilizes the external loop 1428 and the pretied loops 1422 are displaced toward the distal end of the ligator and can be pushed over its end. This method allows extracorporeally pulling the pretied loops over the standing part 1414, once the suture needle 1412 is passed through the tissues and then through the loop 1406 of the guidewire 1408, and after the standing part 1414 has been pulled out of the abdominal cavity using the guidewire 1408. Guidewire 1408 forms a loop 1406 at the distal end. Guidewire 1408 is fixedly attached at the proximal end of suture applier 1402. Further, guidewire 1408 is shown as a dashed line to indicate that it is within the internal channel of shaft 1404. Breakable end 1424 of shaft 1404 may be disconnected from shaft 1404 by breaking shaft 1404 at weakened point 1410. Suture strand 1416 is loaded through aperture 1430 when to assist in backloading the device into an introducer sleeve. An introducer sleeve may be necessary when using other than a trapless cannula.

In the preferred embodiment, a large curved suture needle 1412 is slightly flattened to facilitate its introduction through a size 10 laparoscopic cannula. Of course, other sizes of suture needles may also be used, including small suture needles used for microsurgical procedures that can be performed laparoscopically.

The following discussion details the method in which suture applier 1402 is used. Standing part 1414 is introduced via a cannula into the body cavity along with suture needle 1412. After suture needle 1412 passes through the target tissue, the loop 1406 at the distal end of suture applier 1402 is brought in proximity with suture needle 1412 which is then passed through the loop and cut off the suture after passing two or three centimeters of the suture through the loop 1406. Breakable end 1424 of suture applier 1402 is broken at weakened point 1410 and guidewire 1408 is pulled through shaft 1404 taking with it standing part 1414. Loop 1406 deforms to fit through the internal channel of suture applier 1402.

Standing part 1414 emerges at the proximal end of suture applier 1402, and is pulled such that about three centimeters of standing part suture extends from the distal end of the ligator to the tissues. At this point, pretied loops 1422 may be advanced toward the distal end of suture applier 1402 by pulling on the proximal end of end portion 1416. Pretied loops 1422 will slide of the end of suture applier 1402 in close proximity to the target tissue where the small noose of the knot so formed may be tied and locked by manipulating the suture strands from outside the body cavity, avoiding any significant degree of sawing effect on the tissues. After tying the slip knot, security knots may be added by the surgeon to ensure that the knot does not loosen. One or more hitch knots are fashioned extracarporeally using the standing part of the slip knot which is then introduced through side opening 1418, and 1432. The surgeon holds the suture strands with one hand while advancing the hitch knot with the instrument using the other hand, as previously discussed in relation to FIG. 6.

By moving the pretied loops 1422 along shaft 1404 in this manner, the knot can be formed in close proximity to the target tissues. This knot has a small size noose and as a consequence, less suture material must be drawn through the target tissues, thereby reducing the tissue damage caused by the sawing effect of prior art methods. In addition, the preferred embodiment uses any of the locking knots discussed above, preferably the first Lehrer knot with or without the distal hitch created with step 4. However, the triple hitch (second, third and fourth Lehrer knots) knots should not be used because the pretied loops cannot be advanced over the distal end by pulling the end portion suture. The surgeon may elect to add additional security knots to lock the tie. While delivering the knot to the tissue rather than pulling a large amount of suture material through the tissue to form the knot extracorporeally, a large noose is eliminated which decreases the trauma to the tissues. In addition, the use of additional security knots reduces the total number of suture ligatures required. This, in turn, reduces the total amount of trauma to the tissue.

Figure 15:
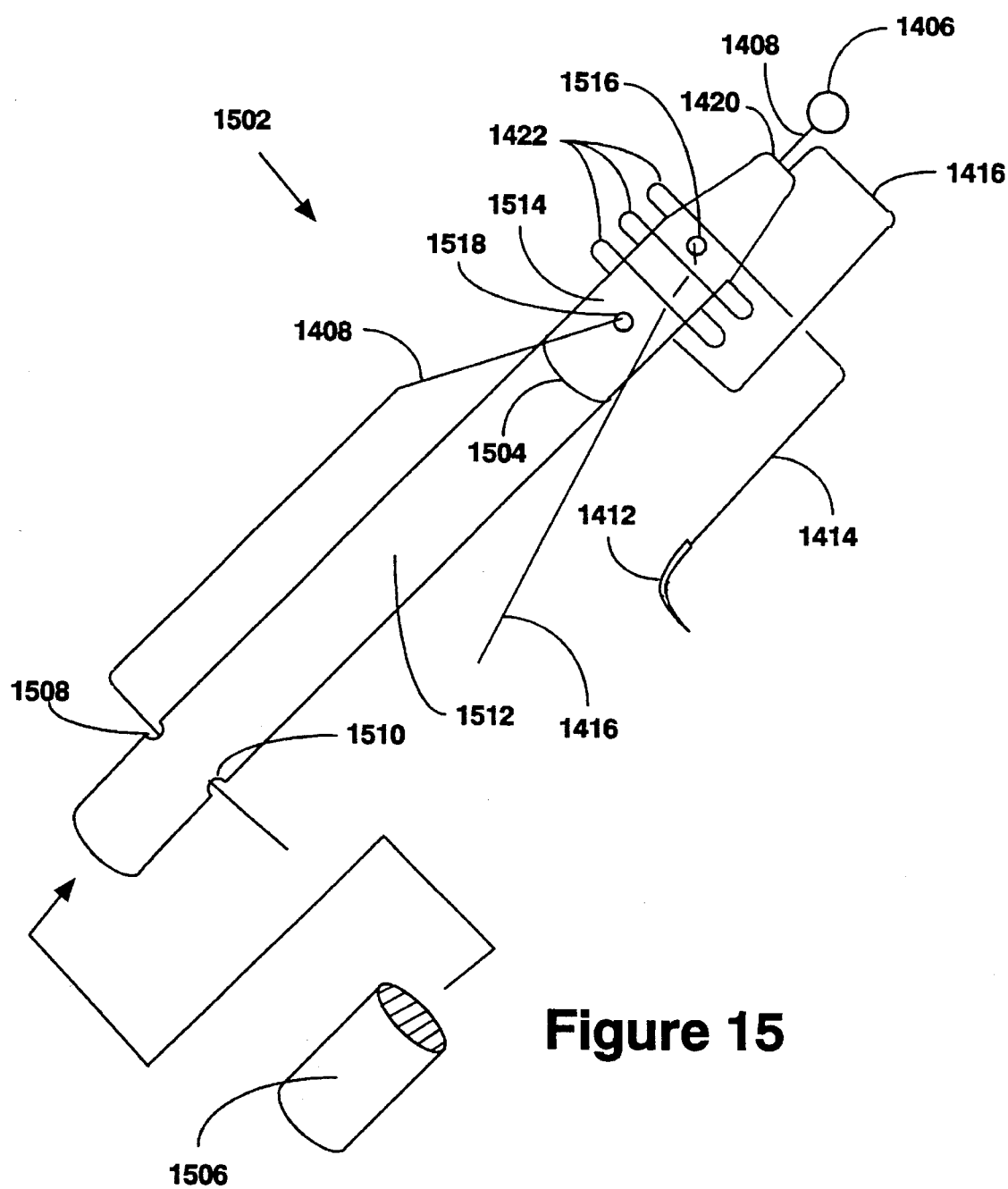
FIG. 15 is an alternative embodiment of the ligator applier in FIG. 14 which has a reusable proximal end.

FIG. 15 shows an alternative embodiment of the suture applier shown in FIG. 14. In this embodiment, the suture shaft is comprised of a reusable proximal end 1512 and a disposable distal end 1514. Proximal end 1512 and distal end 1514 are joined at shaft connection 1504. The two ends of the suture applier 1502 may be joined by any suitable method, such as snap on connectors, screw connectors, etc. In this embodiment, pretied loops 1422 are loaded onto distal portion of the distal end 1514 that is distal to second side opening 1518. End portion 1416 enters the internal channel of distal end 1514 at opening 1420 and exits at opening 1516. Side opening 1516 is one of the two openings of a distal transverse channel in the preferred embodiment, having a second opening (not shown) on the opposite side of the device. Guidewire 1408 enters opening 1420 and exits at opening 1518. For ease of illustration, one internal channel is discussed as well as one distal opening 1406. However, the device can be manufactured with two internal channels and two distal openings for more convenient manipulation of certain types of materials, such as smaller sutures and suture knots. After the disposable distal end 1514 is attached to proximal end 1512, guidewire 1408 is inserted through opening 1508 and exits opening 1510 of proximal end 1512. The free end of end portion 1516 is also inserted through opening 1508 and exits opening 1510 before the surgeon proceeds to backload the ligator into an introducer sleeve (not shown) to enclose loop 1406 in preparation of insertion through the laparoscopic cannula (not shown). Flexible cap 1506 is then slid over proximal end 1512 to hold guidewire 1408 in place. Flexible cap 1506 may be made of any suitable material such as plastic, rubber, or the like, and may be reusable or disposable. Once assembled, the device operates in the same fashion as the embodiment of FIG. 14.

Figure 16A:
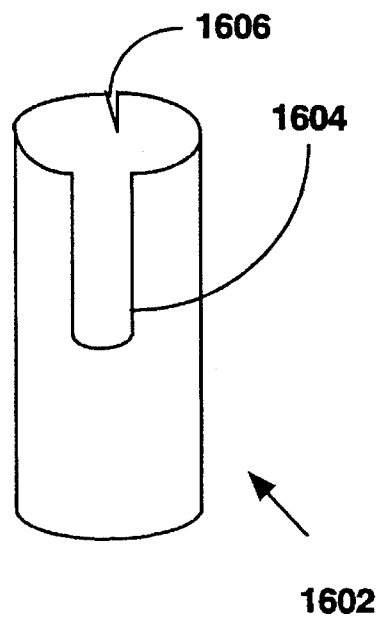
FIGS. 16A–16D are a diagram of a pretied knot spool made with the second Lehrer knot.

The aforedescribed instruments have shown a variety of ways in which the knots disclosed herein may be used. While any of the knots may be tied by hand, it would be advantageous if pretied knots could be mounted quickly on any of the instruments without the delay in the surgical procedure which occurs when knots are hand tied. FIG. 16 discloses a spool 1602 with a pretied knot suture which allows a surgeon to quickly form an extracorporeal slip knot that can then be mounted on the suture appliers disclosed herein. In FIG. 16A, a rear view of spool 1602 is shown without a suture. Spool 1602 is made of any suitable flexible material such as rubber, plastic, etc. Spool notch 1604 is cut out to allow spool 1602 to be manually compressed such that the diameter of spool 1602 can be reduced to allow the pretied loops to slide off the spool. Those skilled in the art will recognize that while a particular notch shape is shown, any shape notch, or any other method of providing for compression of spool 1602 will work as well, so long as the spool holds the knot in the uncompressed state and allows the knot to be slid off in the compressed state.

Figure 16B:
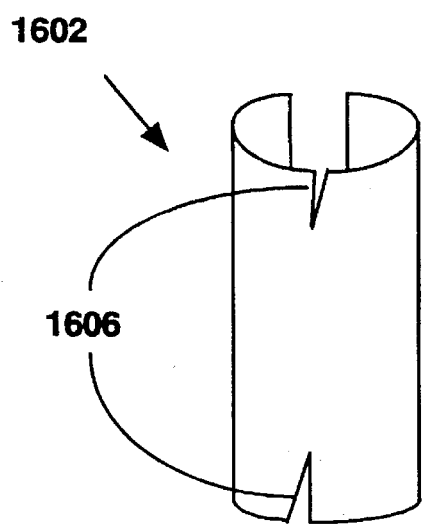

FIG. 16B is a front view of spool 1602. Suture notches 1606 are cut at both ends to hold the suture strands. While notches are used in the preferred embodiment, any suitable method of securing the suture strands is acceptable so long as it does not interfere with the mounting of spool 1602 on any of the needle drivers commonly used in operative laparoscopy; or on the subsequent transfer of the knot from Spool 1602 to the standing part of the suture ligature. Transfer of the extracorporeal slip knot to a suture or ligature applier is discussed more fully below in reference to FIG. 17.

Figure 16C:
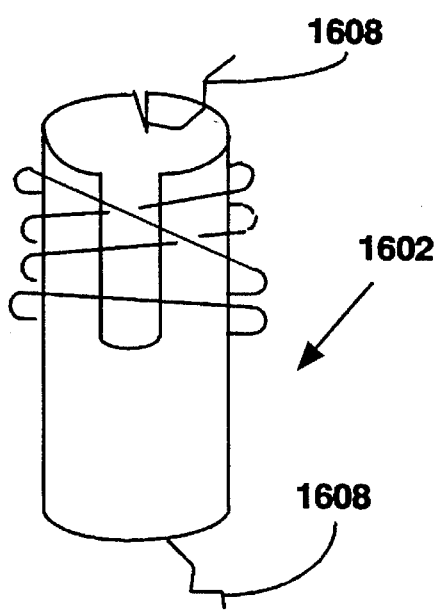
Figure 16D:
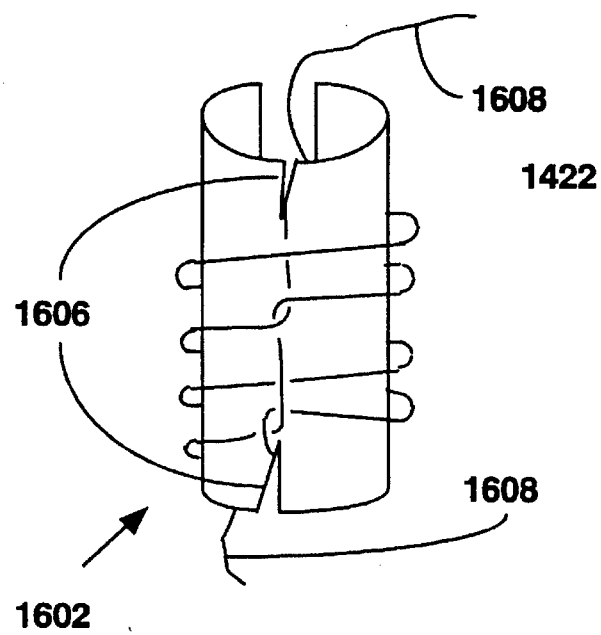

FIG. 16C shows a rear view of the pretied loops of the triple hitched second Lehrer knot 1422 mounted on spool 1602. FIG. 16D shows a front view of the pretied loops of the triple hitched second Lehrer knot 1422 mounted on spool 1602. The suture strands 1608 which extend from knot 1422 are held by notches 1606. Those skilled in the art will recognize that the size and shape of the notches are not important so long as they can hold suture strands 1608 in place. Likewise, the location of the notches on either end is not critical to the invention as they can easily be relocated so long as the strands are held in place. The preferred knot for the spool is one of the Lehrer non-locking or locking slip knots. However, other knots may be employed as well. Spool 1602 may be used with a needle driver. Needle driver is simply inserted into spool 1602. The diameter of spool 1602 in relation to the needle driver is such that it may be compressed after mounting on needle driver. While compressed, pretied loops of knot 1422 may be slid off of spool 1602 onto the standing part suture which can be quickly passed through the pretied loops of the needle driver that was used to remove it through the laparoscopic cannula. The knot is completed extracorporeally, tying the first two distal loops and then loosely closing the other two loops taking care not to accidentally lock the slip knot. The knot is then easily loaded on either model of suture applier 402, 702, 902, 1002, or 1302, thereby reducing the time needed to complete surgery.

FIG. 17A shows an alternative embodiment of the loop ligature applier 1702. Ligator applier 1702 has an internal channel 1710 which when the device is being used as a loop ligator, is occupied by the standing part suture which is attached at the breakable end 1722. In addition, it has a transverse channel 1712 close to the distal end. When the device is being used as a loop ligator, end portion suture 1708 enters the internal channel distal opening 1726 and exits through transverse channel 1712 side opening. In order to tie the slip knot on the tissues, breakable portion 1722 is detached at weakened breakpoint 1728 to pull the standing part suture against the knot that is held at the tip of the ligator 1702. The opening 1712 is smaller than the size of the knot to prevent the knot from entering the internal channel 1710. Care must be taken to defer pulling the end suture 1708 until after the noose has been snugly applied on the tissues to prevent accidentally locking the knot. The end portion 1708 of the suture is used to tighten the knot itself and lock it. This should be the last step in the process of effecting the tie. In the preferred embodiment, one of the ready made Lehrer knots are used. Suture strand 1724 is loaded through aperture 1724 when to assist in backloading the device into a sleeve. A sleeve may be necessary when using other than a trapless cannula.

FIG. 17B shows the device when used in the preferred embodiment as a knot pusher to lock the already tied slip knot with an additional extracorporeal hitch knot. The standing part of the slip knot previously applied is passed through the transverse channel 1712. While holding both ends of the suture 1716, 1708 with one hand, the surgeon pushes knot 1714 forward with the ligator 1702. The standing part of the suture is longer than the end portion of the suture proximal to the hitch knot, and the traject of the sutures through the transverse channel of the ligator is slightly oblique in order to facilitate advancing the hitch knot 1714 toward the tissues.

Compared with prior art devices, such as Ethicon's Pretied Endoknot Suture, the foregoing technique simplifies the formation of the knot outside of the body cavity as follows: A) The looped guidewire and intracorporeal step of passing the suture needle through the loop of the guidewire are eliminated. B) The spool fits over the needle driver and is designed to facilitate forming the slip knot by easily passing the standing part of the suture through the pretied loops and unloading them off the spool. C) The Suture applier introduces and applies the first throw of the suture ligature which uses a locking slip knot which can be effectively locked with the lengthened end portion suture. Additional extracorporeal knots may be applied with the same instrument to further secure the tie as is done in open surgery. Conversely, the prior art ligators are single use devices that cannot be used with hitch knots or as a knot pusher. The first throw made with the slip knot is unlocked and a more time consuming intracorporeal technique to make a security knot is required by the prior art.

While the invention has been described with respect to a preferred embodiment thereof, it will be understood by those skilled in the art that various changes in detail my be made therein without departing from the spirit, scope, and teaching of the invention. For example, numerous small variations can be made on the mechanism employed to accomplish a rotating sheat, a variety of materials can be used to fabricate the suture and ligator appliers, etc.. Likewise, the spool can have many variations so long as it allows the knot to be transferred to the standing part suture by the surgeon. Accordingly, the invention herein disclosed is to be limited only as specified in the following claims.

I claim:

1. A ligator device for extracorporeally manipulating the ends of the two suture strands of a loop ligature or suture ligature knot, comprising:

an internal shaft having a proximal end and a distal end, the internal shaft further comprising at least one indented edge on the surface of the shaft at its distal end and handle means at the proximal end;

an external sheath having a proximal end and a distal end, slidably mounted over the internal shaft, the external sheath further having means to allow insertion of a suture between the external sheath and the indented edge of the internal shaft at the distal end and means to movably attach the external sheath to the handle at the proximal end;

means to selectably enclose suture strands inserted between the external sheath and the internal shaft such that at least one suture strand is slidably grasped and that movement of the suture strand can be selectably controlled extracorporeally; and the proximal end, further comprising control means to control the selective enclosure of suture strands.

2. A ligator device, as in claim 1, wherein the control means further comprises:

first setting means to position the external sheath for loading or removal of a suture; and second setting means to position the external sheath such that a suture loaded between the external Sheath and the indented edge of the internal shaft is slidably enclosed between the internal shaft and the external sheath.

3. A ligator device, as in claim 2, wherein the external sheath further comprises sheath spring contact means;

the handle further comprises retainer means and handle spring contact means;

the control means further comprises entry slot means and control slot means in the proximal end of the external sheath, the entry slot means of a size suitable to slidably accept the retainer means, the control slot means of a size suitable to allow the external sheath to be rotated between the first setting means and the second settings means; and spring means between the sheath spring contact means and the handle spring contact means, the spring means of a size suitable for applying outward pressure between the handle spring contact means and the sheath spring contact means such that when the retainer means is inserted into the control slot means, the outward pressure is exerted on the external sheath to keep the retainer positioned in the selected first or second setting means.

4. A ligator device, as in claim 2, wherein the external sheath further comprises retainer means;

the control means further comprises attachment means suitable to slidably attach to the retainer means and to allow the external sheath to be rotated between the first setting means and the second settings means; and the handle further comprises means to receive the control means, and means to anchor the control means to the handle.

5. A ligator device, as in claim 1, wherein the control means further comprises:

first setting means to position the external sheath for loading or removal of a suture;

second setting means to position the external sheath such that a suture loaded between the external sheath and the indented edge of the internal shaft is slidably enclosed between the internal shaft and the external sheath; and third setting means to position the external sheath such that a suture loaded between the external sheath and the indented edge of the internal shaft is fixedly grasped between the internal shaft and the external sheath.

6. A ligator device, as in claim 5, wherein the external sheath further comprises sheath spring contact means;

the handle further comprises retainer means and handle spring contact means;

the control means further comprises entry slot means and control slot means in the proximal end of the external sheath, the entry slot means of a size suitable to slidably accept the retainer means, the control slot means of a size suitable to allow the external sheath to be rotated between the first, second, and third setting means; and spring means between the sheath spring contact means and the handle spring contact means, the spring means of a size suitable for applying outward pressure between the handle spring contact means and the sheath spring contact means such that when the retainer means is inserted into the control slot means, the outward pressure is exerted on the external sheath to keep the retainer positioned in the selected first, second, or third setting means.

7. A ligator device, as in claim 5, wherein the external sheath further comprises retainer means;

the control means further comprises attachment means suitable to slidably attach the retainer means and to allow the external sheath to be rotated between the first, second, and third setting means;

the handle further comprises means to receive the control means, means to anchor the control means to the handle, and handle spring contact means.

8. A ligator device, as in claim 1, wherein the control means further comprises:

a plurality of setting means to position the external sheath for loading or unloading of at least one suture, for slidably enclosing at least one suture between the internal shaft and the external sheath, or for fixedly grasping at least one suture between the internal shaft and the external sheath.

9. A ligator device, as in claim 8, wherein the external sheath further comprises sheath spring contact means;

the handle further comprises retainer means and handle spring contact means;

the control means further comprises entry slot means and control slot means in the proximal end of the external sheath, the entry slot means of a size suitable to slidably accept the retainer means, the control slot means of a size suitable to allow the external sheath to be rotated between the plurality of setting means and spring means between the sheath spring contact means and the handle spring contact means, the spring means of a size suitable for applying outward pressure between the handle spring contact means and the sheath spring contact means such that when the retainer means is inserted into the control slot means, the outward pressure is exerted on the external sheath to keep the retainer positioned in one of the plurality of setting means.

10. A ligator device, as in claim 8, wherein the external sheath further comprises retainer means; the control means further comprises attachment means suitable to slidably attach the retainer means and to allow the external sheath to be rotated between the plurality of setting means;

the handle further comprises means to receive the control means, means to anchor the control means to the handle; and the handle further comprises means to receive the control means, and means to anchor the control means to the handle.

* * * * *